(12) United States Patent
Osman et al.

(10) Patent No.: US 8,380,286 B2
(45) Date of Patent: Feb. 19, 2013

(54) COMPRESSION DEVICE FOR ENHANCING NORMAL/ABNORMAL TISSUE CONTRAST IN MRI INCLUDING DEVICES AND METHODS RELATED THERETO

(75) Inventors: Nael F. Osman, Baltimore, MD (US); Michael A. Jacobs, Sparks, MD (US); Axel Krieger, San Antonio, TX (US); Ahmed Samir Fahmy, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 586 days.

(21) Appl. No.: 12/308,043

(22) PCT Filed: Nov. 10, 2006

(86) PCT No.: PCT/US2006/043897
§ 371 (c)(1),
(2), (4) Date: Feb. 23, 2010

(87) PCT Pub. No.: WO2007/142678
PCT Pub. Date: Dec. 13, 2007

(65) Prior Publication Data
US 2010/0222667 A1 Sep. 2, 2010

Related U.S. Application Data

(60) Provisional application No. 60/811,155, filed on Jun. 5, 2006.

(51) Int. Cl.
*A61B 5/05* (2006.01)

(52) U.S. Cl. .......... 600/422; 600/407; 600/410
(58) Field of Classification Search .......... 600/407, 600/410, 422
See application file for complete search history.

(56) References Cited

U.S. PATENT DOCUMENTS

| | | | | |
|---|---|---|---|---|
| 5,590,655 | A | * | 1/1997 | Hussman .......... 600/426 |
| 5,833,633 | A | * | 11/1998 | Sarvazyan .......... 600/587 |
| 5,855,554 | A | | 1/1999 | Schneider et al. |
| 2002/0156365 | A1 | * | 10/2002 | Tsekos .......... 600/411 |
| 2003/0007598 | A1 | * | 1/2003 | Wang et al. .......... 378/37 |

* cited by examiner

*Primary Examiner* — Tse Chen
*Assistant Examiner* — Joel F Brutus
(74) *Attorney, Agent, or Firm* — Johns Hopkins Technology Transfer

(57) ABSTRACT

Featured are a device for compression of target tissue while magnetic resonance imaging the target tissue and methods and systems related thereto. The method includes disposing target tissue between the fixed surface and the moveable member of a compression device and compressing the target tissue between the fixed surface and the moveable member. The method also includes acquiring one or more, more specifically a plurality, of sequences of image data of the compressed target tissue using an MRI imaging technique (MRI). In embodiments, the MRI technique is a SENC MRI technique, where tissue encoding is done prior to compressing the tissue and acquiring includes adding a gradient moment in the slice-selection direction to cause demodulation with a specific frequency, hi further embodiments, the sequences of image data are acquired during a single compression and prior to recovery of magnetization.

19 Claims, 15 Drawing Sheets

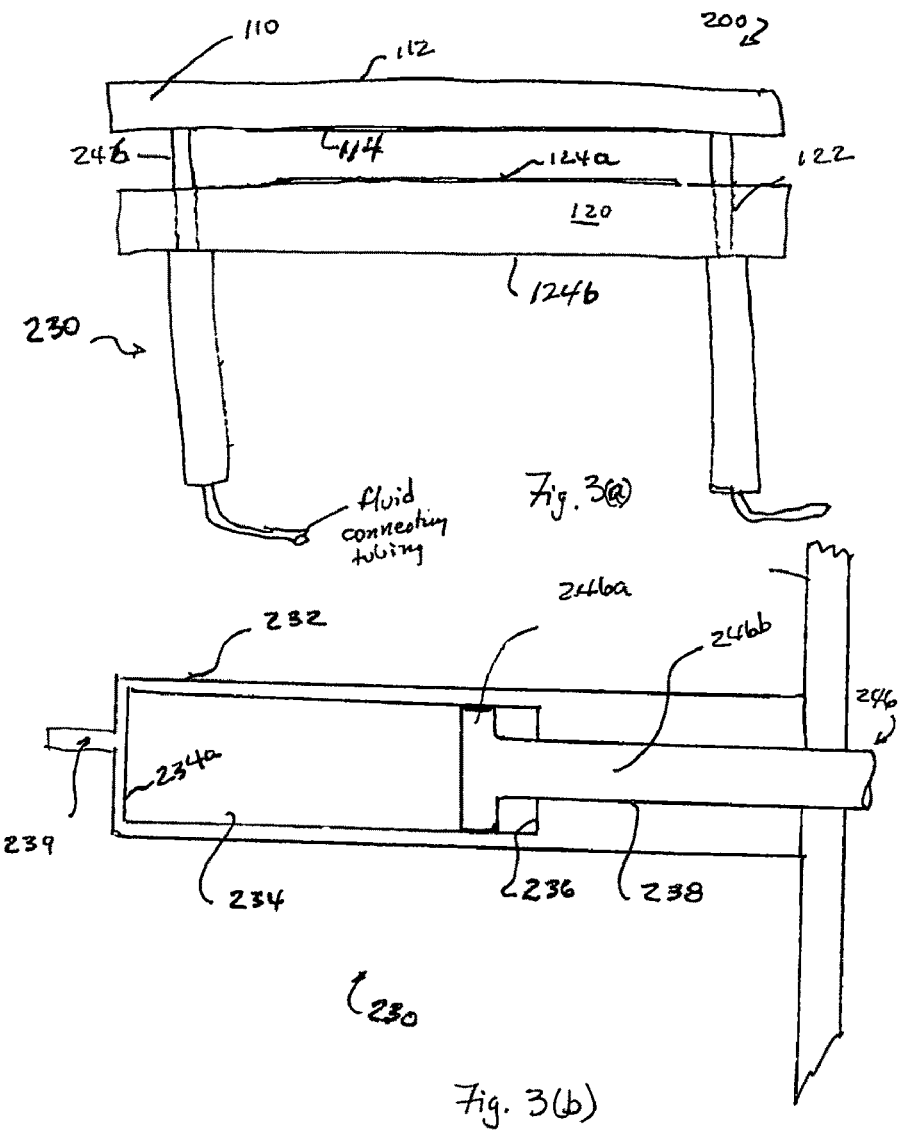
Fig. 3(a)
Fig. 3(b)
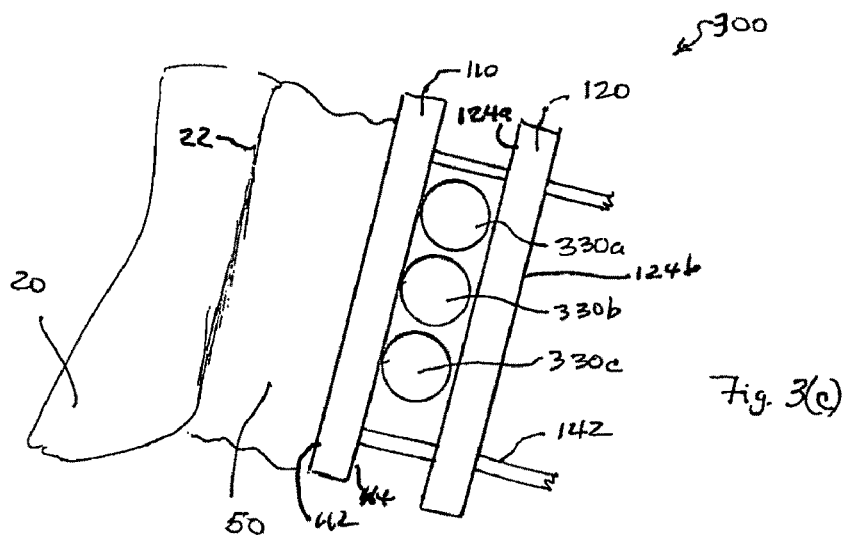
Fig. 3(c)

Fig. 10
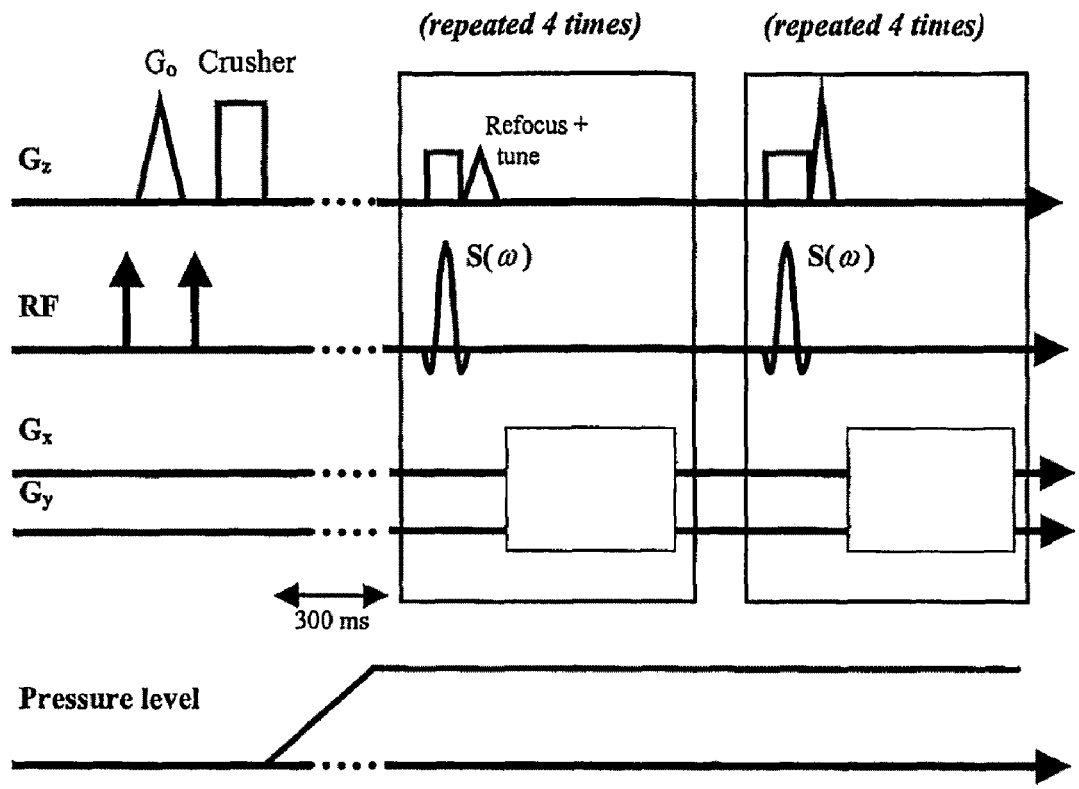
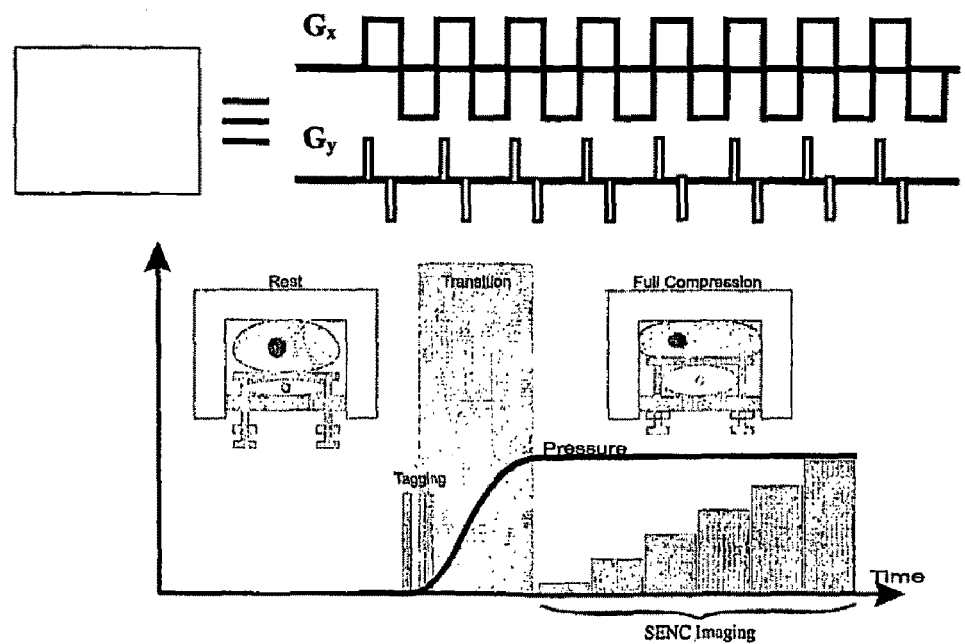
Fig. 9

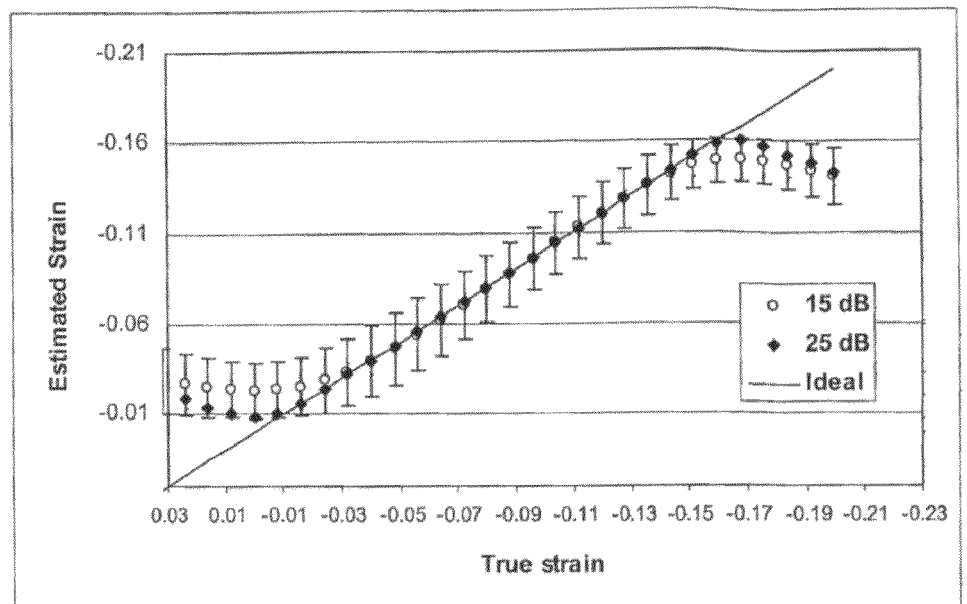
Fig. 13
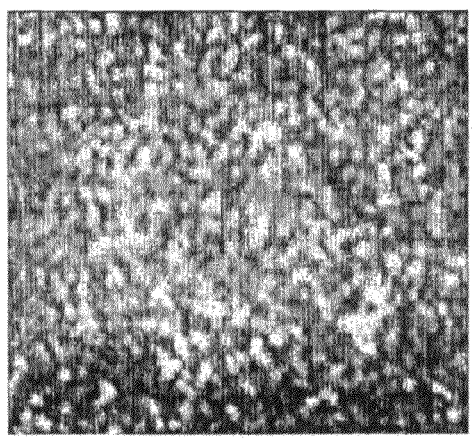 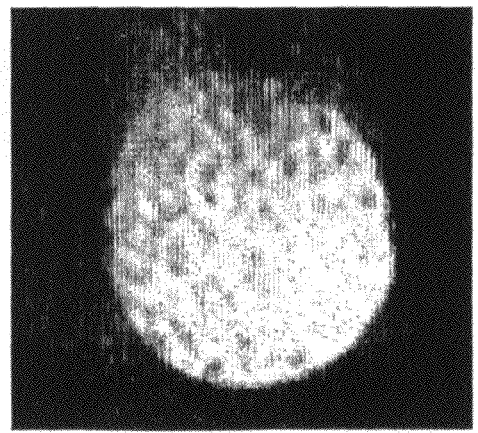
Fig. 14 (a)                           Fig. 14 (b)

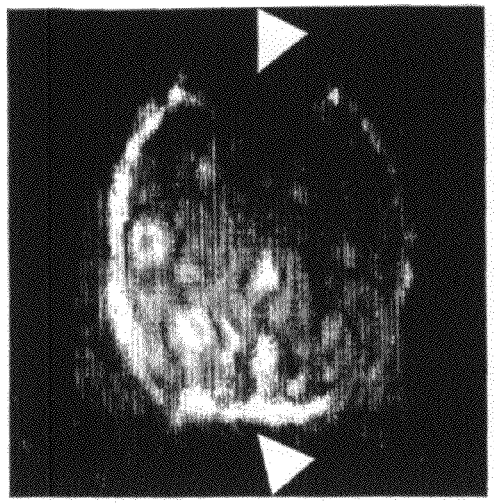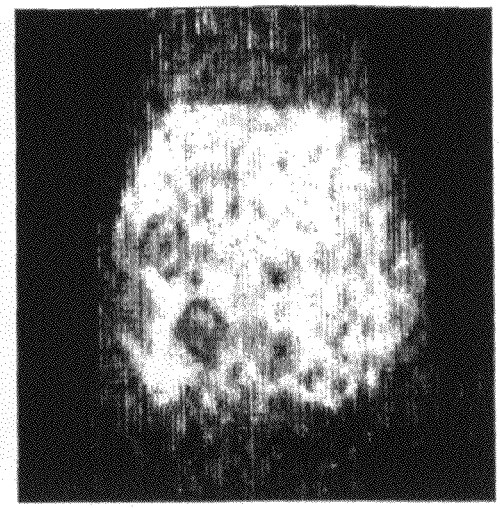
Fig. 15 (a)  Fig. 15 (b)
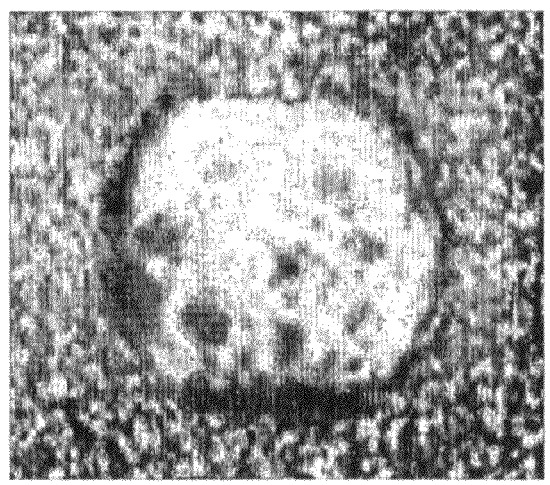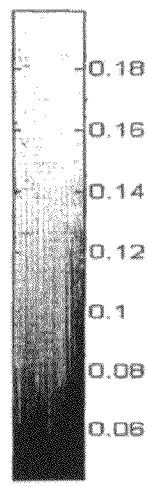
Fig. 16

COMPRESSION DEVICE FOR ENHANCING NORMAL/ABNORMAL TISSUE CONTRAST IN MRI INCLUDING DEVICES AND METHODS RELATED THERETO

This application claims the benefit of U.S. Provisional Application Ser. No. 60/811,155 filed Jun. 5, 2006, the teachings of which are incorporated herein by reference.

FIELD OF INVENTION

The present invention relates in general to techniques for magnetic resonance imaging and devices related thereto, in particular to techniques and devices used to enhance contrast between normal and abnormal tissue, such as for example, tissue of a mammalian breast, and more particularly to compression devices that enhance contrast between normal and abnormal tissue.

BACKGROUND OF THE INVENTION

Breast cancer is the leading cause of death among women 40 to 44 years old, and is one of the leading causes of death in women of age 30 or more. According to the American Cancer Society, it is anticipated that more than 200,000 new cases of breast cancer will be developed in 2006 with approximately 40,000 estimated deaths. "Cancer Facts & Figures 2006, surveillance research," American Cancer Society, Ed.: http://www.cancer.org/, 2006, pp. 4. Breast cancer results from uncontrolled growth of abnormal cells in the breast. The ability of the cancer cells to multiply continuously and spread from the breast to other organs identifies it as "malignant," and potentially life threatening. Due to the rapid growth within a limited space, the cells of the breast cancer accumulate and form a lump that is stiffer than normal. Moreover, due to its irregular growth and extension to the surrounding tissues, malignant tumors usually have irregular borders (e.g., star-shaped).

It is well known that the mechanical properties of tumors are different than those of surrounding normal tissue; for example, some cancerous breast and prostate tumors are harder than normal tissue, or even benign tumors. T. A. Krouskop, T. M. Wheeler, F. Kallel, B. S. Garra, T. Hall, "The elastic moduli of breast and prostate tissues under compression," Ultrason. Imaging, vol. 20, pp. 151-159, 1998. This fact led to the use of tissue stiffness to detect tumors as back as in the time of Hippocrates (460-370 BC), who used manual palpation as a way to detect breast tumors in their early stages. Moreover, because palpation is simple, it is being used today for early cancer detection in the prostate and breast. G. F. Carvalhal, D. S. Smith, D. E. Mager, C. Ramos, W. J. Catalona, "Digital rectal examination for detecting prostate cancer at prostate specific antigen levels of 4 ng/ml or less," J. Urol., vol. 161, pp. 835-839, 1999. Nevertheless, palpation is still a subjective procedure, and detecting tumors that are too deep or too small is still problematic.

Medical imaging modalities were introduced two decades ago and that provide the potential for deep penetration, adequate resolution, and sensitivity. Since stiffness cannot be directly measured, detection of tissue deformation with some type of compression offers an alternative to determine stiffness, particularly if some mechanical model is used. The ultrasound modality has been reportedly used to generate stiffness maps of soft tissues by a technique named elastography. J. Ophir, I. Cespedes, H. Ponnekanti, Y. Yazdi, X. Li, "Elastography: a quantitative method for imaging the elasticity of biological tissues," Ultrason. Imaging., vol. 13, pp. 111-134, 1991. Currently, there are many techniques for elastography that estimate tissue stiffness based on deformation maps measured by ultrasound modalities. In ultrasound elastography, stiffness distribution is estimated by comparing pre- and post-compression deformation parameters of the tissues. A review of these methods can be found in L. Gao, K. J. Parker, R. M. Lerner and S. F. Levinson, "Imaging of the elastic properties of tissue-a review," Ultrason. Med. Biol., vol. 22, pp. 959-977, 1996.

Ultrasound techniques, however, suffer from a number of drawbacks. For example, tissue motion in the axial direction causes alteration of the speckle pattern that needs to be corrected using temporal stretching. Applying large strains, although favorably increasing the strain contrast among the different tissues, may induce irrecoverable distortion of the speckle pattern. J. Ophir, K. A. Alam, B. Garra, F. Kallel, E. E. Konofagou, T. A. Krouskop, and T. Varghese, "Elastography: Ultrasonic estimation and imaging of the elastic properties of tissues," Proc. Inst. Mech. Eng., J. Engng in Medicine, Vol. 213, pp. 203-233, 1999. In addition, the off-axis and elevational tissue motion can severely corrupt the axial-strain estimation by inducing decorrelation noise which requires sophisticated correction. F. Kallel, T. Varghese, J. Ophir and M. Bilgen, "The non-stationary strain filter in elastography. Part II—lateral and elevational decorrelation," Ultrason. Med. Biol., vol. 23, pp. 1357-1369, 1997.

Magnetic Resonance Imaging (MRI) has been introduced as a convenient modality for measuring tissue deformation that can be used to estimate tissue stiffness. N. F. Osman, "Detecting stiff masses using strain-encoded (SENC) imaging," Magn. Reson. Med, vol. 49, pp. 605-608, 2003; C. J. Lewa, J. D. De-Certaines, "MR Imaging of viscoelastic properties," J Magn. Res., vol. 5, pp. 242-244, 1995; T. L. Chenevert, A. R. Skovoroda, M. O'Donnel, S. Y. Emelianov, "Elasticity reconstructive imaging by means of stimulated echo MRI," Magn. Reson. Med., vol. 39, pp. 482-490, 1998; and R. Muthupillai, D. J. Lamos, P. J. Rossman, J. F. Greenleaf, A. Manduca, R. L. Ehman, "Magnetic resonance elastography by direct visualization of acoustic strain waves," Science, vol. 269, pp. 1854-1857, 1995.

MRI can provide features that are difficult or even impossible to implement in ultrasound. For example, MRI-based techniques are capable of direct encoding of 3-D tissue motion with better resolution and SNR as compared to ultrasound techniques. Two main approaches can be utilized in MRI to encode the tissue motion: phase encoding and magnitude encoding. Examples of the first approach include phase-contrast techniques, displacement encoding using stimulated echoes (DENSE) and fast Harmonic Phase (fast HARP) MRI. T. L. Chenevert, A. R. Skovoroda, M. O'Donnel, S. Y. Emelianov, "Elasticity reconstructive imaging by means of stimulated echo MRI," Magn. Reson. Med., vol. 39, pp. 482-490, 1998; R. Muthupillai, D. J. Lamos, P. J. Rossman, J. F. Greenleaf, A. Manduca, R. L. Ehman, "Magnetic resonance elastography by direct visualization of acoustic strain waves," Science, vol. 269, pp. 1854-1857, 1995; T. G. Reese, D. A. Feinberg, J. Dou, V. J. Wedeen, "Phase contrast MRI of Myocardial 3D strain by encoding contiguous slices in a single shot," Magn Reson Med, vol. 47, pp. 665-676, 2002; D. Kim, F. H. Epstein, W. D. Gilson, L. Axel, "Increasing the Signal-to-Noise Ratio in DENSE MRI by Combining Displacement-Encoded Echoes stimulated echoes in cardiac functional MRI," Magn. Reson. Med., vol. 52, pp. 188-192, 2004; and S. Sampath, J. A. Derbyshire, N. F. Osman, E. Atalar, J. L. Prince, "Real-time imaging of cardiac strain using an ultra-fast HARP sequence," in Proc. 9th ISMRM, p. 111, 2001.

The second approach includes MR tagging. E. A. Zerhouni, D. M. Parish, W. Rogers, A. Yang, E. P. Shapiro, "Human heart: tagging with MR imaging—a method for noninvasive assessment of myocardial motion," *Radiology*, vol. 169, pp. 59-63, 1988; and L. Axel, L. Dougherty, "MR imaging of motion with spatial modulation of magnetization," Radiology, vol. 171, pp. 841-845, 1989. An overview of these two approaches/techniques including the advantages and possible disadvantages can be found in C. Ozturk, J. A. Derbyshire, E. R. McVeigh, "Estimating motion from MRI data," IEEE proceedings. Vol. 91. pp. 1627-1648, 2003.

In general, current MRI techniques require multiple compression cycles in order to acquire images with different imaging parameters or to increase the SNR of the images. In addition to the unavoidable prolonged scan times, multiple compressions require a special device to produce exactly the same compression in every cycle, which may hinder the clinical use of these techniques. Moreover, using the phase information to encode the tissue motion necessitates the acquisition of an extra set of phase reference images to correct for the offset phase resulting from BO inhomogeneity. Although the acquisition of a phase reference map is not troublesome when using multiple compression cycles, it constitutes a barrier towards the use of a single compression. T. L. Chenevert, A. R. Skovoroda, M. O'Donnel, S. Y. Emelianov, "Elasticity reconstructive imaging by means of stimulated echo MRI," *Magn. Reson. Med.*, vol. 39, pp. 482-490, 1998; R. Muthupillai, D. J. Lamos, P. J. Rossman, J. F. Greenleaf, A. Manduca, R. L. Ehman, "Magnetic resonance elastography by direct visualization of acoustic strain waves," *Science*, vol. 269, pp. 1854-1857, 1995; T. G. Reese, D. A. Feinberg, J. Dou, V. J. Wedeen, "Phase contrast MRI of Myocardial 3D strain by encoding contiguous slices in a single shot," *Magn Reson Med*, vol. 47, pp. 665-676, 2002; D. Kim, F. H. Epstein, W. D. Gilson, L. Axel, "Increasing the Signal-to-Noise Ratio in DENSE MRI by Combining Displacement-Encoded Echoes stimulated echoes in cardiac functional MRI," *Magn. Reson. Med.*, vol. 52, pp. 188-192, 2004; and S. Sampath, J. A. Derbyshire, N. F. Osman, E. Atalar, J. L. Prince, "Real-time imaging of cardiac strain using an ultra-fast HARP sequence," in *Proc. 9th ISMRM*, p. 111, 2001.

MR tagging encodes the tissue motion by Marking the tissue with alternating bright and dark tag lines than can be tracked and hence depends mainly on the image intensity not the phase. The MR tagging techniques do not require the correction of the background phases, however, because the k-space of a tagged image has a large bandwidth (due to the modulation of the intensity with a highly alternating pattern), acquisition of such images takes longer time than phase contrast or stimulated echo based techniques. Strain-Encoded (SENC) MRI is another technique that uses image intensity to encode the tissue motion. N. F. Osman, S. Sampath, E. Atalar, J. L. Prince, "Imaging Longitudinal Cardiac Strain on Short-Axis Images Using Strain-Encoded (SENC) MRI," Magn. Reson. Med., vol. 46, pp. 324-334, 2001. Unlike conventional MR tagging techniques, SENC MRI is based on stimulated echo acquisition and thus enables rapid acquisition of motion-encoded images. Moreover, generation of strain maps from the acquired images is done faster than the analysis of MR tagged images (including the HARP technique).

Contrast enhanced MR imaging is a sensitive tool to detect breast cancer (a sensitivity of 100% was reported; W. Nunes, M. D. Schnall, and S. G. Orel, "Update of breast MR imaging architectural interpretation model," *Radiology*, vol. 219, pp. 484-94, 2001). Unfortunately, the specificity (wrong-positive cases) of MRI is reported to be low and highly dependent on the imaging, processing, and interpretation technique. For example, specificity values from 37%] to 80% can be found in the literature. Therefore, the challenge in MR breast imaging is to develop methods to minimize false positives and to more easily evaluate and/or localize malignant tumors. L. Esserman, "Integration of imaging in the management of breast cancer," *J Clin Oncol*, vol. 23, pp. 1601-2, 2005.

From many researchers' point of view, data fusion of images acquired from several imaging techniques can be used to increase the specificity of diagnosing breast cancer. M. A. Jacobs, R. Ouwerkerk, A. C. Wolff, V. Steams, P. A. Bottomley, P. B. Barker, P. Argani, N. Khouri, N. E. Davidson, Z. M. Bhujwalla, and D. A. Bluemke, "Multiparametric and multinuclear magnetic resonance imaging of human breast cancer: current applications," *Technol Cancer Res Treat*, vol. 3, pp. 543-50, 2004; M. A. Jacobs, P. B. Barker, D. A. Bluemke, C. Maranto, C. Arnold, E. H. Herskovits, and Z. Bhujwalla, "Benign and malignant breast lesions: diagnosis with multiparametric MR imaging," *Radiology*, vol. 229, pp. 225-32, 2003, and N. Hylton, "Magnetic resonance imaging of the breast: opportunities to improve breast cancer management," *J Clin Oncol, vol.* 23, pp. 1678-84, 2005. One hypothesis is that stiffness images of the examined breast can help confirming the malignancy of a known tumor.

While a number of research efforts have been undertaken in the area of imaging the tissue stiffness using MRI, most MRI techniques require multiple compression cycles in order to acquire images with different imaging parameters or to increase the SNR of the images. Moreover, in some techniques such as the phase-contrast techniques, the use of the phase information to encode the tissue motion necessitates the acquisition of an extra set of phase reference images to correct for the offset phase resulting from BO inhomogeneity. In addition to the unavoidable prolonged scan times, multiple compressions require a special device to produce exactly the same compression in every cycle, which may hinder the clinical use of these techniques. T. L. Chenevert, A. R. Skovoroda, M. O'Donnell, and S. Y. Emelianov, "Elasticity reconstructive imaging by means of stimulated echo MRI," *Magn Reson Med*, vol. 39, pp. 482-90, 1998; R. Muthupillai, D. J. Lomas, P. J. Rossman, J. F. Greenleaf, A. Manduca, and R. L. Ehman, "Magnetic resonance elastography by direct visualization of propagating acoustic strain waves," *Science*, vol. 269, pp. 1854-7, 1995; T. G. Reese, D. A. Feinberg, J. Dou, and V. J. Wedeen, "Phase contrast MRI of myocardial 3D strain by encoding contiguous slices in a single shot," *Magn Reson Med*, vol. 47, pp. 665-76, 2002; D. Kim, F. H. Epstein, W. D. Gilson, and L. Axel, "Increasing the signal-to-noise ratio in DENSE MRI by combining displacement-encoded echoes," *Magn Reson Med*, vol. 52, pp. 188-92, 2004; and A. Manduca, T. E. Oliphant, M. A. Dresner, J. L. Mahowald, S. A. Kruse, E. Amromin, J. P. Felmlee, J. F. Greenleaf, and R. L. Ehman, "Magnetic resonance elastography: non-invasive mappinsg of tissue elasticity," *Med Image Anal*, vol. 5, pp. 237-54, 2001.

It thus would be desirable to provide a compression device, an integrated imaging system embodying such a device and related methods for magnetic resonance imaging that would improve tissue contrast between normal and abnormal tissue. It would be particularly desirable to provide such a device, system and method that could acquire image data during one compression cycle and prior to recovery of magnetization in comparison to prior art devices, systems and methods. It also would be desirable to provide such a device, system and method in which the tissue compression and acquisition of image data can be controlled in such a way as to minimize manual intervention and control by a clinician or technician.

Such compression devices preferably would be simple in construction and such methods would be less involved than conventional methods.

SUMMARY OF THE INVENTION

The present invention features a device for compression of tissue to be imaged, systems and apparatuses for imaging tissue using MRI techniques using such a compression device. Also featured are methods related to or embodying such devices, systems or apparatuses.

A compression device according to the present invention includes a moveable member including a contact surface that is configured to contact the target tissue and a member moving mechanism operably coupled to the moveable member, the mechanism including means for moving the moveable member with respect to a fixed surface disposed opposite to the moveable member contact surface, whereby the target tissue is compressed between the moveable member contact surface and the fixed surface. Also, the moveable member and the member moving mechanism are made of MRI-compatible materials. In addition, such a compression device includes a stationary member and the member moving mechanism moves the moveable member with respect to the stationary member. Further, the fixed surface is one a surface of a second stationary plate, a surface of a skeletal structure or a surface of a structure for an MRI detection coil. The compression device is particularly adaptable for the compression of breast tissue while the breast is disposed within a conventional MRI breast coil.

In further embodiments, the moving means is a fluid moving means that causes the moveable member to move with respect to the fixed surface and/or the stationary member responsive to the application of fluid pressure to the fluid moving means. In exemplary embodiments, the fluid is one of a liquid or a a gas, such as air. In yet further embodiments, the fluid moving means is a pneumatic moving means.

In more particular embodiments, the moving means includes one or more expandable members disposed between the moveable member and the stationary member, each of the one or more expandable members being configured so as to expand primarily in one direction when fluid pressure within each expandable member is increased. In yet more particular embodiments, the moving means includes one or more expandable members disposed between the moveable member and the stationary member, each of the one or more expandable members being configured so as to expand primarily in one direction when the pneumatic pressure within each expandable member is increased.

In further embodiments, the moving mechanism includes a force limiting mechanism that limits the compressive force being applied to the target tissue. In an illustrative embodiment, the force limiting mechanism includes one or more sliding members secured to the moveable member and a stop affixed to at least one of the one or more sliding members, the stop being affixed to the sliding member so as to be a predetermined distance from the moveable member. The predetermined distance is established so as to limit movement of the moveable member and thus so the force being applied to the target tissue during compression is less than or equal to a desired value.

In further embodiments, the force limiting mechanism further includes one or more through apertures in the fixed member, one aperture for each of the one or more sliding members, wherein the sliding members and the fixed member through apertures are arranged so that each sliding member is slidably received in a through aperture. Also, the stop affixed to at least one of the one or more sliding members is disposed opposite to a back surface of the stationary member. When the at least one stop contacts the back surface further sliding movement of sliding members is restrained thereby limiting or stopping movement of the moveable member. In more specific embodiments, the force limiting mechanism includes a plurality of sliding members and a plurality of stops, a stop being affixed to each sliding member.

In yet further embodiments, the force limiting mechanism is a fluid device that limits a maximum fluid pressure developed for compression. Such a fluid device is a relief valve or pressure regulating valve that limits the maximum fluid pressure. It also is within the scope of the present invention for an open/closed type of valve to comprise the force limiting mechanism, where operation of the valve is controlled so as to stop the flow of fluid increasing pressure. In yet further embodiments, the compression device further includes a pressure sensor that senses pressure of the fluid.

In yet further embodiments, the compression device further includes a controller that is configured to control operation of the member moving mechanism and for providing one or more output signals as input to the MRI process. Such a controller can include a computer or digital processor and software for execution on the computer/digital processor, which software includes instructions, criteria and code segments for controlling operation of the device and preferably also synchronizing operations of the device and the magnetic resonance imaging process.

In particular embodiments, the controller controls flow of fluid to each of the one or more expandable members so as to thereby control the expansion of the one or more expandable members. More particularly, the controller is configured to cause fluid to flow to each of the one or more expandable members to move the moveable member with respect to the stationary member and to terminate fluid flow when a desired expansion of the one or more expandable members is achieved and so as to maintain the pressure in each of the one or more expandable members. Also, the controller is configured so as to cause fluid to flow from each of the one or more expandable members, so as to thereby reduce the compressive force on the target tissue. Also, it is within the scope of the present invention for a switch to be interconnected to the controller, which switch is operable by the patient and provides an output signal to the controller when so activated. In this way, if the compressive pressure on the tissue is creating excessive discomfort or the like to the patient, an output signal is provided to the controller which in turn can stop flow of fluid to the one or more expandable members and/or also cause fluid to flow from each of the one or more expandable members, so as to thereby reduce the compressive force on the target tissue.

In another aspect of the present invention, there is featured a system for imaging target tissue of a patient, which includes a magnetic resonance imaging (MRI) apparatus that images the target tissue using magnetic resonance imaging techniques and a tissue compression device that selectively compresses the target tissue, such as the compression device hereinabove described. Such a system also includes a controller operably coupled to the tissue compression device and the MRI apparatus, the controller being configured to control operation of the member moving mechanism and for providing one or more output signals as input to the MRI process so the compressed targeted tissue is imaged during a compressed tissue condition. In particular embodiments, the compressed tissue condition corresponds to condition where the controller terminates fluid flow to the one or more expandable members when a desired expansion of the one or more expandable members is achieved and so as to maintain the pressure in each of the one or more expandable members.

In yet further aspects of the present invention, there is featured a method for imaging tissue. Such an imaging method includes providing a tissue compression device that selectively compresses target tissue, such as the compression device described herein and disposing the target tissue between the fixed surface and the moveable member. After so disposing the target tissue, the imaging method further includes compressing the target tissue between the fixed surface and the moveable member and providing an output signal to an MRI imaging apparatus so image data is acquired after establishing a tissue compressed condition. Thereafter, the imaging method includes acquiring one or more sequences of image data of the compressed target tissue using an MRI imaging technique (MRI), one or more of MRI imaging parameters being adjusted so as to be different for each of the one or more sequences of image data being acquired.

In more particular embodiments, the MRI imaging technique is a Strain Encoded (SENC) MRI technique, in which tissue encoding is done prior to said compressing the target tissue and said acquiring includes adding a gradient moment in the slice-selection direction to cause demodulation with a specific frequency. Also, the imaging method includes acquiring a plurality of sequences of image data during a single compression of the target tissue and prior to recovery of magnetization.

Other aspects and embodiments of the invention are discussed below.

Definitions

The instant invention is most clearly understood with reference to the following definitions:

The term "tissue" is used herein in its broadest sense and thus shall be understood to include an aggregate of cells usually of a particular kind together with their intercellular substance that form one of the structural materials of an animal including human beings. In general, there are four basic types of tissue in the body of all animals, including the human body and lower multicellar organisms such as insects, and these include nervous tissue, muscle tissue, epidermal, and connective tissue. These compose all the organs, structures and other contents. It also should be recognized that term "tissue" as used herein shall not be understood to be limited only to one of the types of tissue but also can include a body part that is composed of more than one type of tissue (e.g., muscle tissue and epidermal).

BRIEF DESCRIPTION OF THE DRAWING

For a fuller understanding of the nature and desired objects of the present invention, reference is made to the following detailed description taken in conjunction with the accompanying drawing figures wherein like reference characters denote corresponding parts throughout the several views and wherein:

FIG. 3(a) is a top view of another tissue compression device of the present invention without fluid system components for clarity;

FIG. 3(b) is a cross-sectional view of a part of the tissue compression device of FIG. 3(a);

FIG. 3(c) is an illustrative view showing tissue compression using a skeletal part and yet another tissue compression device of the present invention;

FIG. 9 is a graphical view showing the sequencing of MRI image acquisition and tissue compression;

FIG. 10 is a time line illustration of a segmented EPI implementation of SENC MRI, where the sequence starts with a 1-1 SPAMM tagging, followed by two image acquisitions (note also the increment of the tuning gradient from the first to the second image);

FIG. 13 is a graphical plot of the estimation error of strain in the presence of noise (negative strains represent contraction), for the sake of clarity, error bars (mean square error) are shown only for the 15 dB curve (worst case noise);

FIGS. 14 (a),(b) are illustrations of two images acquired without compression with tuning frequencies: (a) 0.53 mm$^{-1}$ (FIG. 14(a)) and (b) 0.62 mm$^{-1}$ (FIG. 14(b));

FIGS. 15(a),(b) are illustrations of phantom images acquired after applying compression to the object in a direction perpendicular to the image plane using a tuning frequency of (a) 0.53 mm$^{-1}$ (FIG. 15(a) and (b) 0.62 mm$^{-1}$ (FIG. 15(b)), where the arrowheads show signal void areas caused by phantom over-stretching;

FIG. 16 is an illustration of a strain map obtained by combining the two SENC images in FIGS. 15 (a),(b) by first applying Equation 2 to estimate the local tagging frequency followed by Equation 3 to calculate the strain (units are in mm/mm);

DESCRIPTION OF THE PREFERRED EMBODIMENT

Figure 1:
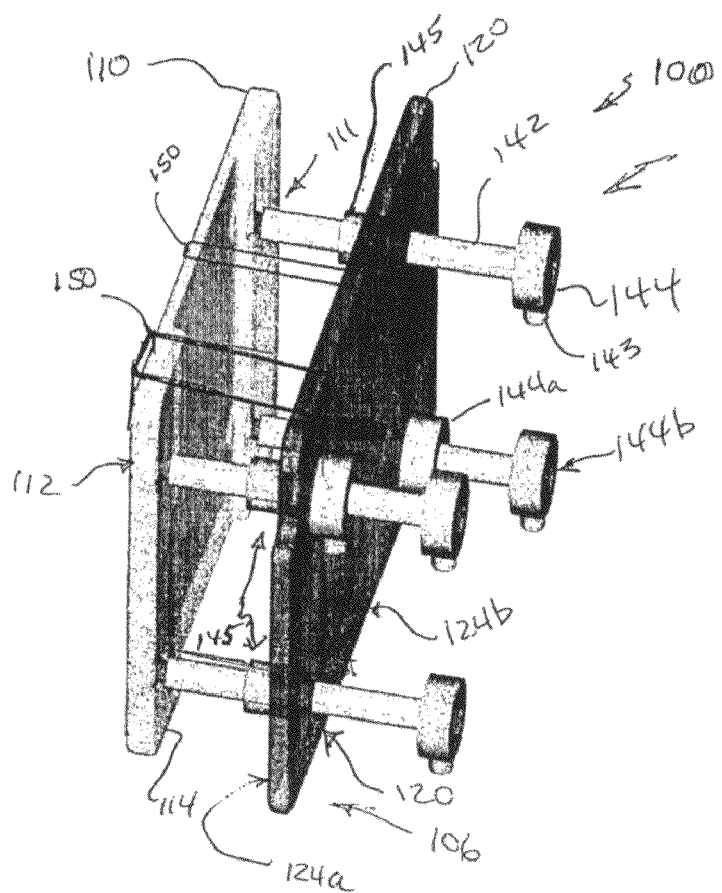
FIG. 1 is a perspective view of a tissue compression device of the present invention without the moving mechanism and fluid system components for clarity.
Figure 2:
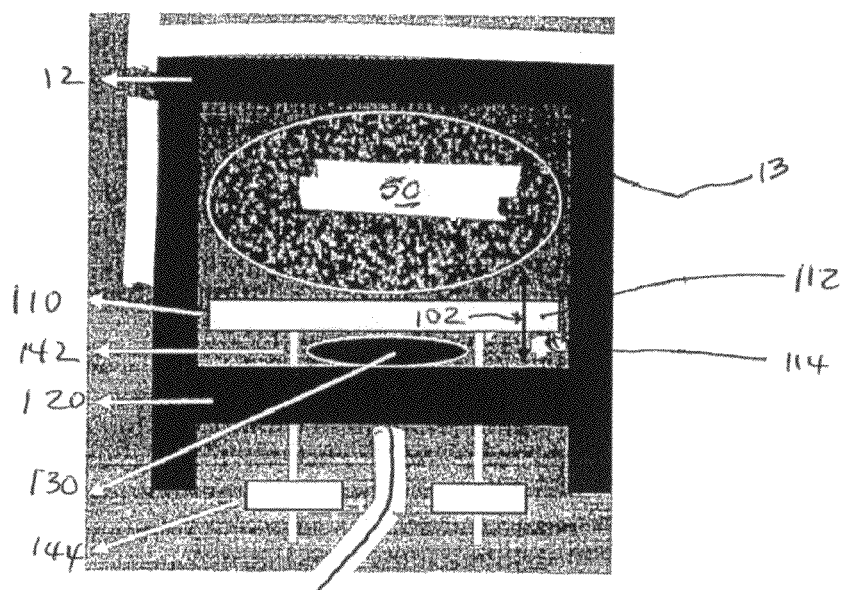
FIG. 2 is a schematic view illustrating placement of a body part or target tissue for compression using a compression device according to an embodiment of the present invention.
Figure 4A:
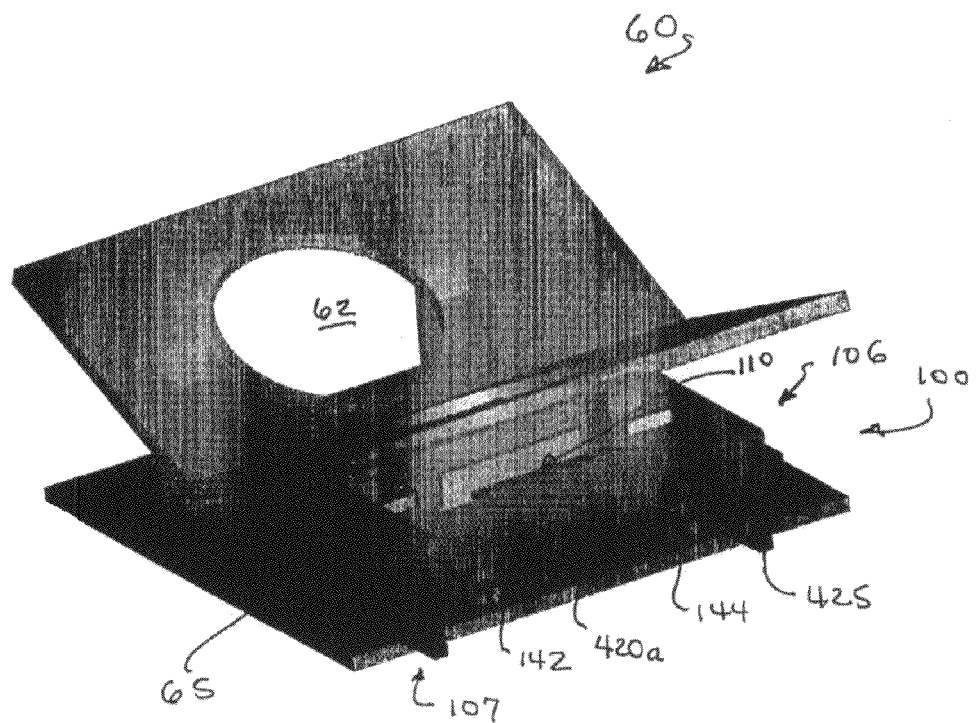
FIGS. 4(a)-(c) are various perspective views of a tissue compression device and a conventional MRI breast detection coil.

Referring now to the various figures of the drawing wherein like reference characters refer to like parts, there is shown in FIGS. 1-2 a perspective view and a schematic view respectively of a tissue compression device 100 according to the present invention alone or in combination with a portion of a conventional magnetic resonance imaging (MRI) coil used for imaging of breast tissue (hereinafter referred to as a "breast coil" 60; FIG. 4(a)).

Such a tissue compression device 100 includes stationary or non-moving structure 106, a moveable member 110 and a moving mechanism 130 that is disposed between the non-moving structure and the moveable member. The moving mechanism 130 is generally configured and arranged so that it causes the moveable member to move in a direction 102 that is generally away from the non-moving structure 106 and towards a surface of a fixed structure such that tissue 50 disposed between the moveable member 110 and the fixed structure surface (such as that shown illustratively in FIG. 2) is compressed therebetween. As discussed further herein, such compression is preferably accomplished in a controlled manner so that the amount of compression is controlled so as to be at or below a desired amount of compression.

In particular aspects of the present invention, the tissue compression device 100 or compression device, is particularly configured so as to be used in combination with a magnetic resonance imaging (MRI) apparatus or MRI systems so that the tissue can be imaged using any of a number of MRI techniques while the tissue is in the compressed state. Thus, the materials selected for use with those portions of the tissue compression device 100 that are in the field of view or located with the effect of the main magnet are MRI acceptable materials as well as those being otherwise acceptable for the intended use (e.g., bio-compatible). Such materials include plastics such as plexiglass or a product sold by General Electric under the name ULTEM. Those portions of the compression device 100 which are not within the field of view or within the effect of the main magnet can be constructed of any of a number of materials that are known in the art and otherwise appropriate for the intended use.

In particular embodiments, the non-moving structure 106 of the tissue compression device 100 includes a stationary member 120 and the moveable member 110 is moveably (e.g., slidably) coupled to the stationary member. The stationary member 120 is secured to the other structure 107 (FIG. 4(a)) of the non-moving structure 106 using any of a number of techniques known to those skilled in the art. Such other structure 107 can be used to secure the non-moving structure so the tissue compression device 100 is maintained in fixed relation to the magnetic field generating and signal detecting elements of the MRI apparatus while acquiring image data.

As described herein, in further embodiments, the non-moving structure 106 or the other structure thereof is adjustable so that the tissue compression device 100 can be adjusted to accommodate different size body parts.

The stationary member 120 also is arranged so that a front surface 124a thereof opposes a back surface 114 of the moveable member and so the moving mechanism 130 is disposed in the region between the stationary member front surface and the moveable member back surface. In the illustrated embodiment, the moving mechanism is a fluid inflatable type of device which at least moves in a given direction responsive to an increased fluid pressure or increased volume of fluid within the device. The fluid is one of a liquid or a gas, such as air. Alternatively, as shown in FIG. 3(c), the moving mechanism can comprise a plurality of such moving mechanisms 130a-c.

In an exemplary embodiment, the moving mechanism 130 is a balloon or bag type of device that inflates or expands responsive to the increase in pressure or volume of the liquid or air being introduced therein. In further exemplary embodiment, the moving mechanism can comprise one such device as shown in FIG. 2 or a plurality of such devices as shown in FIG. 3(c). It also contemplated and thus within the scope of the present invention for any of a number of devices known to those skilled in the art to be disposed between, and operably coupled to, the moveable member 110 and stationary member 120. Such other devices being such that a force is applied to the moveable member 110 so as to cause it to move in a direction away from the stationary member 120. Such other types of devices include, but are not limited to, any of a number of devices embodying hydraulic or fluid operating principles, such as for example, a hydraulic or pneumatic piston. In particularly preferred embodiments, the moving mechanism 130 uses a fluid such as a gas (e.g., air) or other fluid having acceptable MRI characteristics. The fluid components interconnected to the moving mechanism 130 as well as the controls over such fluid components are described hereinafter.

Such a tissue compression device 100 also preferably is configured and arranged so as to include one or more compressive force limiting mechanisms that are provided to limit the compressive force that can be generated and applied to the tissue when it is being compressed. There is shown in FIGS. 1-2, one such force limiting mechanism 140 that includes at least one sliding member 142 and at least one stop 144 secured to the at least one sliding member. In further embodiments, the force limiting mechanism includes a plurality of sliding members 142 and the at least one stop 144 is secured to one of the plurality of sliding members. Alternatively, a plurality of stops 144 are provided one for each of the sliding members.

In yet further embodiments, a plurality of stops 144a,b are provided for at least one of the sliding members 142. In this embodiment, one of the stops 144b acts as an final stop to prevent any further movement while the other stop 144a is adjustable stop. Thus, if the adjustable stop 144a slides along the sliding member 142 when a compressive force is being applied, the final stop 144b provides further assurances against inadvertent over-compressing of the tissue.

The sliding member 142 is mechanically coupled to the moveable member 110 using any of a number of techniques known to those skilled in the art (e.g., adhesives, vibration welding, and threaded connections). In the illustrated embodiment, the moveable member 110 is configured with a threaded connection 111 so that the sliding member 142 is threadably secured to the moveable member. The connection established between the sliding member 142 and the moveable member 110 preferably is strong enough to withstand the operational forces created when the movement of the moveable member is stopped.

Each of the at least one stops 144 is secured to a sliding member 142 a predetermined distance from the moveable member back surface 114. The predetermined distance is established so as to limit the distance the moveable member 110 can travel in a direction away from the stationary member 120 and thus, limit or control the compressive force that can be developed and applied to the tissue. In one embodiment, the stop 144 is removably secured to the sliding member 142 such as, for example, by a set screw 143 threadably disposed in the stop and that also mechanically engages the sliding member (e.g., exterior surface thereof). In another alternative embodiment, the stop 144 is fixedly secured to the sliding member 142 (e.g., vibrational welding, adhesives, etc.) and the sliding member is removably secured to the moveable member 110. For this embodiment, the travel distance would be adjusted by using a stop and sliding member combination that would provide the desired travel distance.

In either of these described embodiments, the clinician can adjust the travel distance of the moveable member 110 so as to compensate for different size body parts and also, so the amount of compression can be generally maintained at an acceptable level for different size body parts. As indicated herein, it also is contemplated that the stationary structure 106 of the tissue compression device 100 can be adjusted with respect to structure of the magnetic resonance coil so as to compensate for different size body parts. It thus, also is contemplated that a clinician can compensate for different size body parts by adjusting the stationary structure and/or by adjusting the travel distance of the moveable member 110.

Each of the sliding members 142 also is preferably movably received in a through aperture 122 in the stationary member 120 and so that the stop 144 is disposed generally opposite to a back surface 124b of the stationary member. In this way, the sliding member 142 moves longitudinally within the aperture 122 as the moveable member 110 is moved by the moving mechanism 130. Such movement continues until the stop 144 contacts or engages the stationary member back surface 124b. When the stop 144 contacts the stationary member back surface 124b, further longitudinal movement of the sliding member is stopped, thereby limiting further travel of the moveable member 110.

Disposing the sliding members 142 in the stationary member through apertures 122 also generally controls or guides the movement of the moveable member 110 as it is being moved by the moving mechanism 130. In this way, the moveable member preferably moves in a direction generally away from and orthogonal to the stationary member front surface 124a.

In yet further embodiments, the tissue compression device 100 includes one or more intermediate stops 145, more particularly a plurality of such intermediate stops. An intermediate stop 145 is arranged on the sliding members 142 and so as to be between the stationary member front surface 124a and the moveable member back surface 114. In particular embodiments, the intermediate stop is slidable on the sliding member 142. The intermediate stop 145 is sized and shaped so as to maintain a predetermined spacing between the stationary member front surface 124a and the moveable member back surface 114 when the moving mechanism 130 is deactivated or when the movable member 100 is located in proximity to the stationary member 120, also corresponding to the rest state of the tissue.

In further embodiments, the tissue compression device 100 includes a member returning mechanism 150 that is configured and arranged with respect to the moveable member 110 to facilitate the movement of the moveable member away from the fixed surface and/or towards the stationary member 120. The member returning mechanism 150 can be any of a number of devices or techniques know to those skilled in the art that can cause the moveable member to move in a direction away from the fixed surface when the fluid pressure is decreased. For example, the member returning mechanism 150 comprises a fluid operated piston or a spring like member can be operably coupled to structure of the tissue compression device and positioned and operably coupled to the moveable member 110 so as to cause such motion towards the stationary member 120. In an illustrated embodiment, the member returning mechanism 150 comprises one or more resilient members that are operably coupled to and between the moveable member 110 and the stationary member 120. The one or more resilient members also are arranged such so that when the moving mechanism 130 moves the moveable member 110 in a direction from the stationary member 120 a restoring force is created to return the moveable member to a condition corresponding to the tissue rest condition when the pressure is release.

Although flat surfaces are shown or depicted for each of the moveable member 110 and the stationary member 120, this shall not be construed as limiting the present invention to such surfaces. It is within the scope of the present invention, for the moveable member front surface 112 to be configured or shaped to optimize contact and compression within the limits imposed by particular MRI technique. It also is contemplated that the moveable member 110 as well as the front surface 112 thereof to be configured so as to minimize potential for injury to the tissue being compressed (e.g., rounding edges, smoothing front surface for example to eliminate sharp edges/ridges/points).

It also is within the scope of the present invention, for the moveable member back surface 114 and the stationary member front surface 124a to be configured so as to optimize the force developed by the moving mechanism 130 and so the force being applied to the tissue is generally uniform across the moveable member front surface 112. These surfaces 114, 124a, also are configurable so as to limit movement of the moving mechanism with respect to these surfaces in directions other than where the moving mechanism moves the moveable member. Also, although the sliding members 142 are depicted as being generally in the form of a cylindrical rod, this is not limiting, as a sliding member can have any number of geometric shapes as is known to those skilled in the art and otherwise appropriate for the intended use (e.g., can be a t-shaped rod).

According to one aspect of the present invention, and as shown in FIG. 2, the body part (e.g., female mammalian breast) including the tissue, to be compressed is located between a surface 13 of the structure 12 of the MRI detection coil 10, which forms a fixed surface, and the moveable member front surface 112. With such an arrangement, when the moveable member 110 is moved by the moving mechanism 130, the tissue is compressed between the coil fixed surface 13 and the moveable member front surface 112 such as shown pictorially in FIG. 9.

Referring now to FIG. 3(a) there is shown a schematic view of another tissue compression device 200 according to the present invention that includes a moveable member 110, a stationary member 120, and a moving mechanism 230 including a sliding shaft member 246. Reference should be made to the foregoing discussion regarding the stationary and moveable members 120, 110. There also is shown in FIG. 3(b), a cross-sectional view of the moving mechanism 230, the sliding shaft member 246, and the stationary member 120.

On end 246 (c) of each sliding shaft member 246 (see FIG. 3(a)) is secured to the moveable member 110 so that longitudinal movement of the sliding shaft members 246 in direction 102 (FIG. 2) causes the moveable member to move away from the stationary member 120 so as to thereby compress the tissue 50 (FIG. 2) much in the same manner as described above for the compression device 100 shown in FIGS. 1-2. This end 246(c) can be secured to the moveable member 110 using any of a number of techniques known to those skilled in the art, including that described above for securing the limiting mechanism sliding member 142 to the moveable member 110.

The other or enlarged end 246(a) of the sliding shaft member 246 is movably disposed within the housing 232 of the moving mechanism 230. As more clearly shown in FIG. 3(b), the moving mechanism housing 232 is arranged so as to include a chamber 234 that extends lengthwise to an end 236 forming a stop surface, and an aperture 238. The shaft portion 246(b) of the sliding shaft member 246 is movably received in the housing aperture 238 and the enlarged end 246(b) is movably received in the housing chamber 234.

In further embodiments, the enlarged end 246(a) and the inner surface of the chamber 234 are configured and arranged to cooperate to form a sliding seal therebetween. In this way, when fluid is admitted into the portion of the chamber between the enlarged end 246(a) and the chamber end 234(a) including the fluid port 239, the enlarged end 246(a) moves longitudinally away from the fluid port chamber end 234(a) towards the housing stop surface end 236. The stop surface end 236 can form a stop to limit further travel of the sliding shaft member 246 in the longitudinal direction when the enlarged end 246(c) contacts stop surface end 236.

Referring now to FIG. 3(c) there is shown a tissue compression device 300 according to yet another aspect of the present invention in which the tissue is compressed between a surface 22 of the skeletal structure 20 (e.g., bone) of the body part being imaged so that this skeletal structure surface in effect forms a fixed surface opposite to the moveable member 110. According to this aspect of the invention, the body part including the particular tissue to be imaged is located between the moveable member 110 of the compression device 300 and the skeletal structure surface 22. Thus, when a moving mechanism 330a-c is actuated to move the moveable member 110, the tissue is compressed between the skeletal structure surface 22 and the movable member front surface 112.

As also indicated above, FIG. 3(c) also illustrates an embodiment in which a plurality of moving mechanisms 330a-c, are located between the moveable member back surface 114 and the stationary member front surface 124a. In this arrangement, each of the a plurality of moving mechanisms 330a-c would be actuated so as to cause the moveable member to move.

Figure 3D:
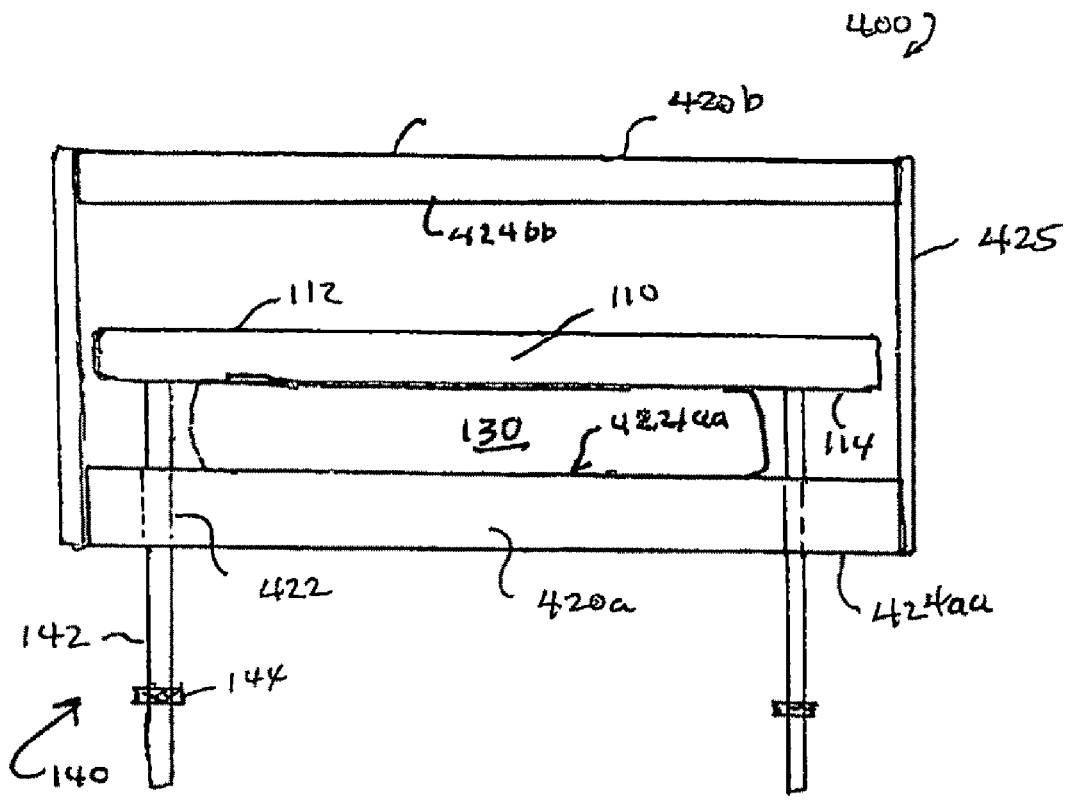
FIG. 3(d) is a top view of yet another tissue compression device of the present invention without fluid system components for clarity.

Referring now to FIG. 3(d) there is shown a tissue compression device 400 according to yet another aspect of the present invention in which the tissue compression device 400 includes a first and second stationary members 420a,b which are disposed on either side of the moveable member 110 and which are maintained in fixed relation to each other such as for example by the cross-structure 425. The cross-structure 425 is any of an number structural arrangements as is known to those skilled in the art or easily obtained using well known engineering principles that interconnects the first and second stationary members 420a,b as described herein. Reference also should be made to the foregoing discussion regarding the stationary and moveable members 120, 110 for details of the moveable member 110, the limiting mechanism 140 and the first and seconds stationary members 420a,b not otherwise provided below.

The first stationary member 420a like the stationary member 120 described above, includes a front surface 424aa, a back surface 4242ab and through apertures 422. As with the above, the sliding members 142 are movably received in the through apertures 422 and the stops 144 contact the back surface 424ab to limit travel of the sliding members and thus the moveable member 110. Also, the moving mechanism 130 is disposed between the moveable member back surface 114 and the stationary member front surface 424aa.

The second stationary member 420b is arranged with respect to the moveable member so that the back surface 422bb of the second stationary member is spaced from and opposite to the moveable member front surface 112. In this arrangement, the body part having the tissue 50 to be imaged is located between the second stationary member back surface 422bb and the moveable member front surface 112. Thus, when the moving mechanism 130 is actuated to move the moveable member 110, the tissue is compressed between these two surfaces.

Figure 4B:
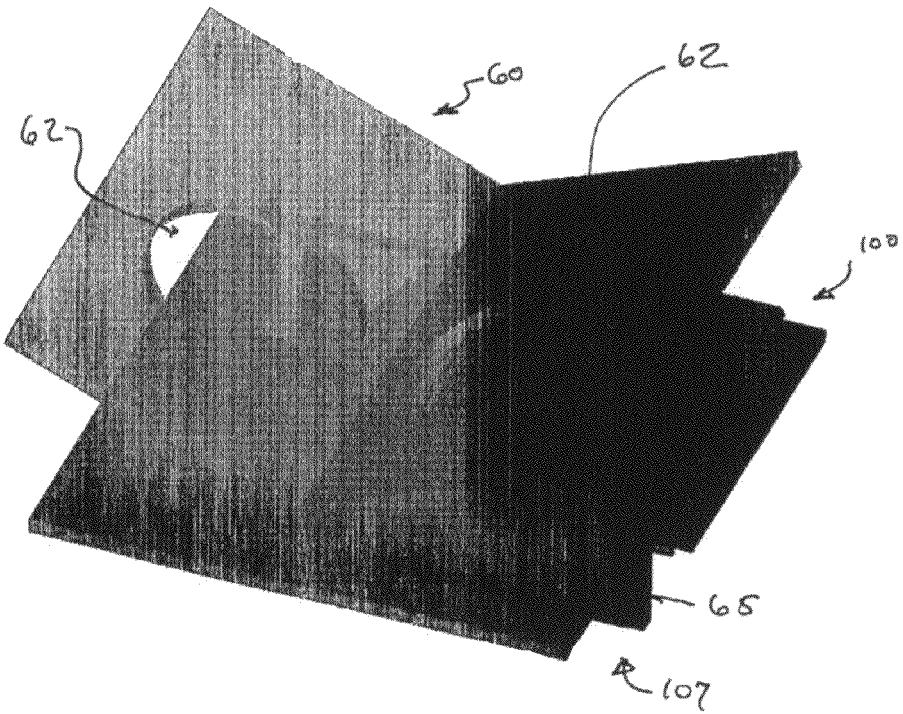
Figure 4C:
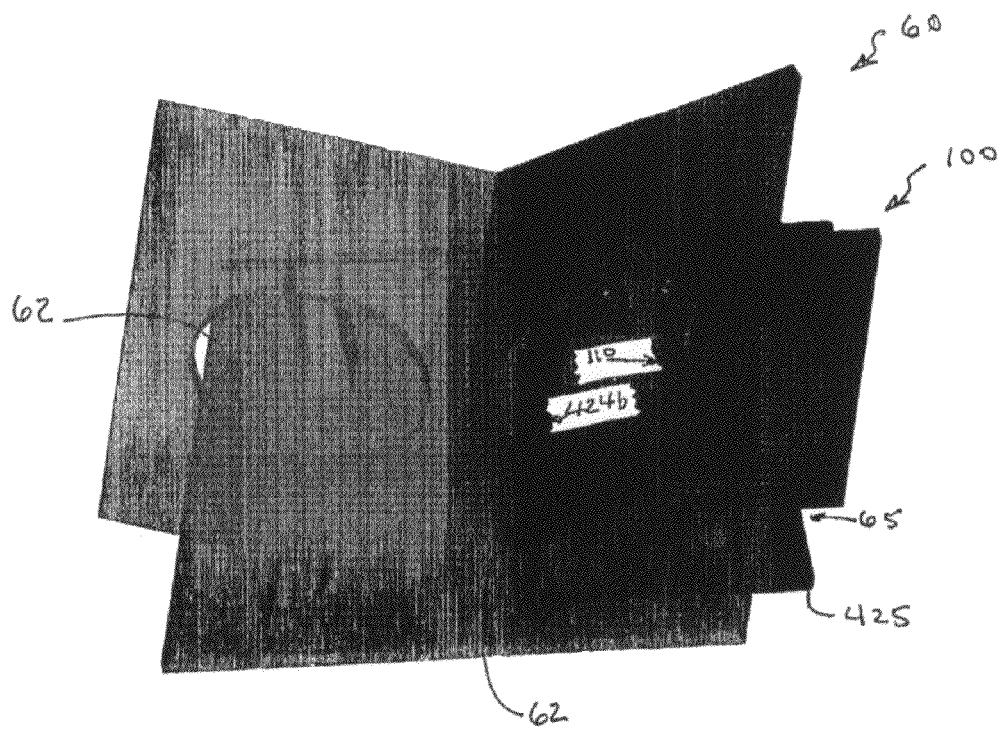

In further embodiments and with reference also to FIGS. 4(a)-4(c), the cross-structure 425 can be configured so the structure 106 including the moveable member 110 and the first stationary member 420b is selectively secured to the cross-structure. In this way, the structure 106 including the moveable member 110 and the first stationary member 420b is moveable with respect to the second stationary member 420b and thus, the distance between the moveable member back surface 422bb and the moveable member front surface 112 can be adjusted to accommodate or compensate for different size body parts. For example, the cross-structure 425 can include a plurality of through holes 65 that are spaced along the length of the cross-structure through which a bolt or the like passes and secures the structure 106 including the moveable member 110 and the first stationary member 420b to the cross-structure. By using a different through hole, the distance can be adjusted.

The foregoing are illustrative of some examples of moving mechanisms that are adaptable for use with a tissue compression device of the present invention. Such examples are not limiting as the tissue compression device can be adapted for use with any of a number of devices or use any of a number of techniques known to those skilled in the art which can move the moveable member in the desired fashion including use of components that are powered by other than fluids. Such other components can include the use of pizeo-electric motors or stepping electric motors that can selectively drive the moveable member 110 away from or towards the fixed surface and/or the stationary member 120.

Figure 3E:
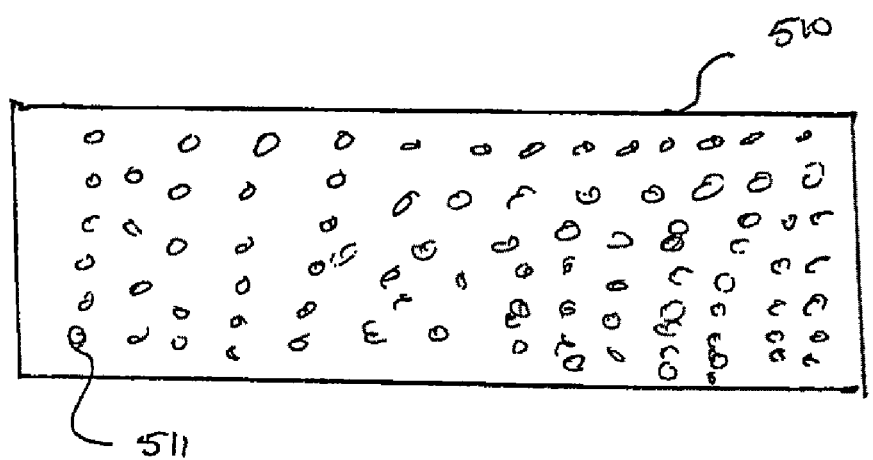
FIG. 3(e) is a front view of a surface of a moveable member configured to allow tissue biopsy.

As is known to those skilled in the art, it is common practice to perform a biopsy in conjunction with an imaging process so that samples can be acquired for suspect tissue. In the case of breast examinations conducted using MRI techniques, the structure of the MRI detection coil can include a plurality or a multiplicity of apertures. In such an arrangement, a biopsy needle is passed through the aperture and inserted into the body part so as to acquire the tissue sample. Thus, and as shown in FIG. 3(e), the moveable member 510 according to the present invention also can be configured so as to include a plurality or a multiplicity of apertures 511 which can be used for purposes of biopsy. As is known to those skilled in the art, other structure of the tissue compression device 100, for example, the stationary member 120 or the first and second stationary members 420a,b, also are similarly configured to include a plurality or a multiplicity of through apertures so the end of biopsy needle can pass through each of the stationary member and the moveable member.

As indicate herein, a tissue compression device 100, 200 of the present invention is particularly adaptable for use with a conventional breast detection coil 60. Referring now to FIGS. 4(*a*)-(*c*) there is shown various views of a tissue compression device 100 according to the present invention secured to a conventional breast coil 60. In use a breast of the patient is inserted through each of the two openings 62 in the coil 60 so that the breast tissue would be is disposed between the moveable member 110 and a fixed structure of the coil or the second stationary member 420*b*. In this way, and as described herein, the moveable member 110 can compress the breast tissue. Although a single tissue compression device 100 is shown, it should be recognized that two tissue compression devices can be secured to the breast coil, where each compression device would be arranged with respect to one of the openings 62. As also shown in these figures the structure of the conventional coil can be easily adapted for insertion and securing the tissue compression device thereto.

Figure 5:
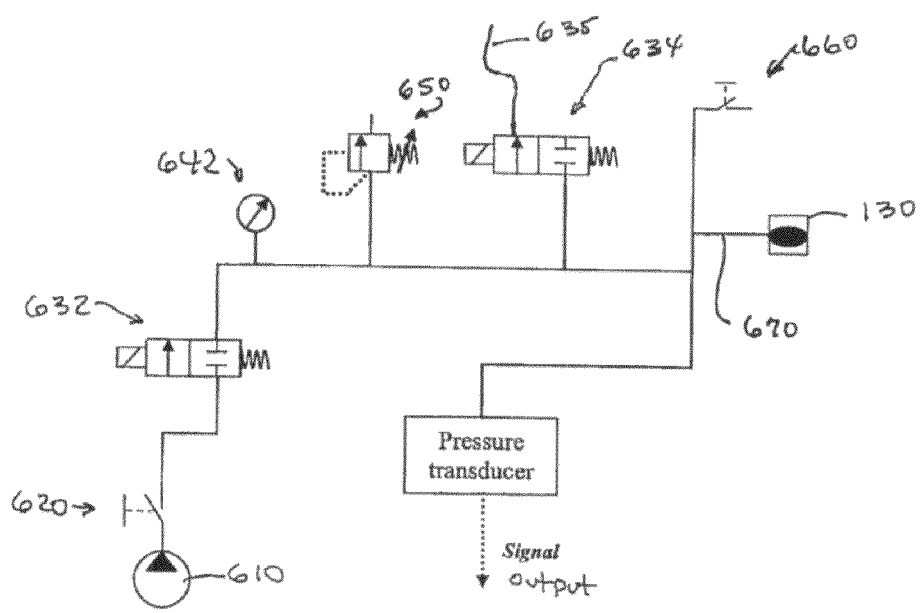
FIG. 5 is a schematic view of an exemplary fluid system that forms a portion of a tissue compression device according to the present invention.

In illustrated exemplary embodiments, the moving mechanism 130 preferably embodies fluid (e.g., hydraulic, pneumatic) components that are used to control movement by the moving mechanism as well as providing mechanisms for controlling or limiting the compressive force being developed and applied to the tissue to be imaged. Referring now to FIG. 5, there is shown a schematic view of an exemplary fluid system 600 that forms a portion of a tissue compression device 100 according to the present invention and also any of the embodiments described herein.

The fluid system 600 is interconnected to the moving mechanism 130 or to each of one or more moving mechanisms 330*a-c* (see FIG. 3(*c*)) by interconnecting tubing 670. The fluid system 600 includes a fluid source 610, first and second valves 632, 634 that control the fluid flow to/from the moving mechanism 130, a pressure transducer 644 that provides an output signal as hereinafter described to control timing of the imaging process, the interconnecting tubing 670 and system tubing 605. In further embodiments, such a fluid system 600 further includes an operator actuated switch 620, a pressure gauge 642, a relief valve 650 and a patient switch 660. The system tubing 605 fluidly couples the fluid source 610 to the interconnecting tubing 670 as being fluidly coupled to other components of the fluid system 600 (e.g., pressure transducer).

As a tissue compression device 100, 200, 300, 400 of the present invention can be used in combination with MRI systems, and as some of the materials embodied in fluid system components are not typically MRI compatible materials, portions of the fluid system 600 and/or the components thereof are located distal or away from the main and gradient magnets/magnetic coils of the MRI system. In more particular embodiments, some portions of the fluid system 600 are located in areas that are remote from the MRI main and gradient magnets, for example in the room where the technician controls the scanning/imaging operations or from centralized locations in a facility.

In an illustrative embodiment the fluid source 610 is the centralized fluid or gaseous source for an entire facility that includes facility interconnecting piping or tubing with a one or more discharge ports located throughout the facility. In such a case, one of the discharge ports would be appropriately fluidly coupled to the fluid system 600 so that the centralized fluid or gaseous source is fluidly coupled to the fluid system. In an exemplary illustrative embodiment, such a fluid source 610, or the centralized fluid source, includes a pump or a pump coupled to one or more storage tanks.

The interconnecting tubing 670 and the system tubing 605 is any of a number of tubing or piping products known to those skilled in that art, that are suitable for the intended use. As portions of the interconnecting tubing 670 are likely to be within the influence of the MRI main magnet, it is preferable that at least these portions of the interconnecting piping be made of an acceptable MRI material (e.g., plastic). The other portions of the interconnecting piping 670 can be made of the same material or of another material that is suitable for the intended use, such as the material used for the system tubing (e.g., a plastic or metal such as copper).

As indicated above the fluid system includes first and second valves 632, 634 that control the flow of fluid to/from the moving mechanism 130. The first and second valves 632, 634 are any of a number of valves or valve like products known to those skilled in the art which selectively open and close a flow path so as to allow or prevent fluid from flowing therethrough, which valves are otherwise appropriate for the intended use. In exemplary embodiments the first and second valves 632, 634 are a solenoid type of valve. The first valve 632, is fluidly connected to the system tubing 605 so as to selectively open and close the system tubing that fluidly couples the fluid source 610 to the moving mechanism 130.

After the imaging process is completed, the compressive force on the tissue 50 should be released to facilitate removing the body part from the tissue compression device 100. In the event that the volume to be imaged cannot be imaged in the time available, then the compressive force on the tissue also may have to be released so another image acquisition as described herein can be performed. The second valve 634, is fluidly coupled to the system tubing 605 so a vent pathway 635 is selectively fluidly coupled to the system tubing that is fluidly coupled to the moving mechanism 130.

The vent pathway 635 can comprise the open end of the valve or short length of tubing that discharges to atmosphere if the fluid is a gas that can be discharged to atmosphere. If discharge to atmosphere is not possible or desired, then the vent pathway 635 is appropriately fluid coupled to a receptacle (e.g., container) that receives the fluid being discharged. Thus, when the pressurized fluid within the moving mechanism 130 is to be released, the fluid can be vented through the vent pathway 635 thereby reducing fluid volume and pressure within the moving mechanism, which in turn would allow the moveable member 110 to move in a direction away from the fixed surface 22 and towards the stationary member 120. As described below in connection with FIG. 6, the first valve 632 and second valve 634 also are operably coupled to a controller 740 that controls the operation of the first and second valves.

The pressure transducer 644 is operable coupled to the system tubing 605 so as to be capable of detecting the fluid pressure in the system tubing 605. More particularly, the pressure transducer 644 is positioned in the portion of the system tubing 605 that is downstream of the first valve 632. In this way, the pressure transducer 644 continuously monitors and provides an output corresponding to the fluid pressure in this downstream portion of the system tubing 605 including the first valve 632, including when the moving mechanism 130 moves the moveable member 110 to compress the tissue 50. The pressure transducer 644 also can be any of a number of devices that also outputs a signal when a predetermined set point is reached. The pressure transducer 644 is operably coupled to a controller 740 (see FIG. 6) so that such pressure signals are continuously monitored and evaluated by the controller. This monitoring and evaluation process is described further below in connection with FIG. 6.

The fluid system 600 also includes a relief valve 650 that is preferably connected to the system tubing 605 downstream of the first valve 632 and upstream of the moving mechanism 130. The relief valve 650 is any of a number of safety or relief valves known to those skilled in the art and appropriate for the fluid medium in the system tubing 605. The relief valve 650 is provided to regulate the pressure in the portion of the system tubing upstream of the relief valve 650 and so as to maintain the fluid pressure in this portion of the system tubing as well as that of the fluid within the moving mechanism at or below a set pressure. The set pressure is preferably set so as to provide another mechanism for limiting the compressive force being applied on the tissue 50 by the moveable member 110 as well as preventing the fluid pressure from exceeding desired values in the event that the fluid pressure is not being regulated in the intended manner (e.g., failure of first valve to close). The discharge or vent line from the relief valve 650 is appropriately routed and configured based on the fluid medium (see also discussion above regarding the vent pathway 635 from the second valve 634).

It should be recognized that other valves that are not shown may be fluidly coupled to the system piping to satisfy local building safety codes as well as other system considerations. For example, a pressure regulator type of valve may be installed between the fluid source 610 and the first valve 632 to reduce the pressure of the fluid coming from the fluid source so that it less than a predetermined value consistent with the established pressure limits for the fluid components of the fluid system 600. Also, local building codes may require that a safety relief valve be installed between the fluid source and the first valve 632. While not shown the addition of such valves into the fluid system 600 of the present invention is well within the skill of those in the art and need not be described further herein.

The fluid system 600 also can include a pressure gauge 642 that is disposed in the system tubing 605 downstream of the first valve 632. In this way, a manual or visual reading of the pressure in the portion of the system tubing 605 downstream of the first valve can be obtained as a back up or in addition to the system pressure as being outputted by the pressure transducer 644.

The fluid system 600 also can include an operator actuated switch 620 and a patient switch 660. Although the patient switch 660 is shown schematically as being coupled to the fluid system for diagrammatic purposes, this need not be the case. The patient switch 660 is provided so that if the compressive force being applied to the tissue of the patient is such as to cause pain or extreme discomfort to the patient, the patient can actuate the patent switch 660 so as to cause the fluid pressure in the system tubing 605 from increasing and/or to be reduced. The patient switch 660 is any of a number of manual switches as is known to those skilled in the art that is appropriate for the intended use and operation.

This pressure reduction can be accomplished in any of a number of ways. In one illustrative embodiment, the actuation of the patient switch 660 opens a vent pathway, so that fluid in the system tubing 605 flows through the vent pathway thereby reducing system pressure. In another illustrative embodiment, the actuation of the patient switch 660 causes a signal to be outputted to the controller 740 (see FIG. 6). The controller 740 in turn outputs signals to any of the first and second valves 632, 634 so to reduce the fluid pressure and either terminate the pressurization and imaging process or continue the process but where the tissue imaging is done at the reduced pressure.

The operator actuated switch 620 is disposed downstream of the fluid source 610 and upstream of the first valve. The operator actuated switch 620 is any of a number of manual switches as is known to those skilled in the art that is appropriate for the intended use and operation. In use, the operator actuated switch 620 is a normally closed switch. In this way, the operator actuated switch 620 is not opened to allow fluid flow, until the operator intentionally actuates the switch so as to start the compression and imaging process. As the technician operating the tissue compression device and the imaging system is likely to be in the room where the scanning apparatus (e.g., main and gradient magnetic coils) is located when the patient is being prepared for the scanning process, an inadvertent activation of the first valve 632, for example, should not cause the moveable member 110 to move. In further embodiments, the operator actuated switch 620 is configured so as to require continuously actuation by the operator during the compression and imaging process.

Figure 6:
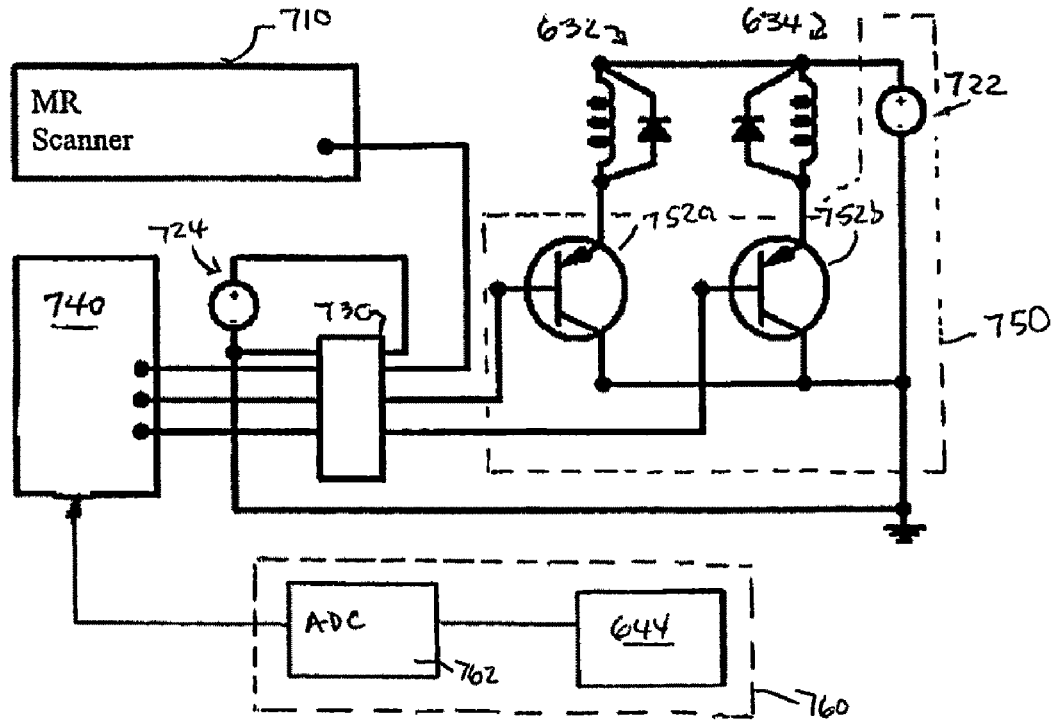
FIG. 6 is a circuit diagram that illustrates an electrical and electronic module of an integrated system according to the present invention.

Referring now to FIG. 6, there is shown a circuit diagram of an electrical and electronic module 700 of an integrated system according to the present invention. For convenience of description, the electrical and electronic module 700 is described as if it where formed of three main parts. The electrical and electronic module 700 also includes two power supplies 722 and 724, a buffer chip 730, and a controller 740 that is operably coupled to the three main parts, the buffer chip 730 and an MRI scanner 710.

The controller 740 is any of a number of devices known to those skilled in the art, that can control the functionalities of the electrical and electronic module 700 and thus control functionalities of the compression device 100, 200. The controller 740 also is preferably configured so as to as provide output signals to the MRI scanner to synchronize the MRI related functionalities with the compression of tissue 50 by the compression device 100, 200. In particular embodiments, the controller 740 is a computing device as is known in the art including one or more software or applications programs being executed therein to carry out the monitoring and control functions as herein described. More particularly, the controller 740 includes a microprocessor, memory operably coupled to the microprocessor, storage for storing data and the applications programs, I/O ports, input devices (e.g., keyboard, mouse) and a display.

The first part of the electrical and electronic module 700 is a control circuit 750 for the first and second valves 632, 634, which includes two power transistors 752a,b to drive respectively one of the first and second valves upon receipt of the appropriate control signal (e.g., a low-power signal) from the controller 740. In an exemplary illustrative embodiment, the signal from the controller 740 passes first through a buffer chip 730 in order to isolate the controller 740 (e.g., controller I/O ports) from the power transistor for electrical protection.

In this way, the controller 740 can send a control signal to one power transistor 752a to cause the first valve 632 to open while the second valve is maintained closed thereby causing the tissue 50 to be compressed by the tissue compression device 100. Thereafter, the controller 740 can send a signal to the first power transistor 752a to cause the first valve 632 to close while the second valve is maintained closed so as to maintain a steady state pressure condition while acquiring image date of the compressed tissue. After completion of imaging of the compressed tissue, a stage of such imaging, or for some other reason (e.g., actuation of the patient switch 660, see FIG. 5), the controller 740 can send a control signal to the other power transistor 752b to cause the second valve 634 to open while the first valve is maintained closed thereby causing or allowing the moveable member 110 to be moved away from the tissue (e.g., remove the compressive force).

The second part of the electrical and electronic module 700 is the pressure signal acquisition circuit 760. This circuit is composed of the pressure transducer 644 that senses the pressure inside the fluid system 600 (see FIG. 5) and converts it to an analog voltage signal and an Analog-to-Digital (ADC) converter 762 that converts the analog voltage signal produced by the pressure transducer 644 to a digital signal (e.g., an 8-bit digital signal). The digital signal is inputted to the controller 740. In an exemplary illustrative embodiment, the ADC converter 762 has a latched tri-state outputs (e.g., an ADC0809 (National Semiconductor). In this embodiment, there is no need to add a buffer or a latch between the ADC and the controller I/O ports. It should be recognized that it is within the scope of those skilled in the art to adapt the circuitry described herein using any of number of techniques or other components known to those skilled in the art.

As described herein, the digital signal is continuously monitored and evaluated by the controller 740 to determine if the pressure within the fluid system 600 has reached a desired value corresponding to the desired compressive force or has exceeded a desired safety limit-which requires actions be taken to reduce fluid pressure. As also described herein, such signals also are utilized by the controller 740 to determine when signals are to be outputted to the MRI scanner 710.

The third part of the electrical and electronic module 700 is a buffered connection between a I/O port of the controller 740 and an input (e.g., the ECG input) of the MRI scanner 710. This output signal is used to synchronize the MRI related pulse sequence(s) with the actuation of the moving mechanism 130 (e.g., inflation of the airbag). The output signal or pulse is generated by a piece of computer software being executed in the controller 740 and has the shape controlled duty cycle and frequency appropriate for the MRI scanner 710. In illustrative embodiments, when the output signal is an ECG signal, the pulse has the shape of square wave with controlled duty cycle and frequency.

As discussed herein, the controller 740 provides the output signals to the MRI scanner 710 when it is determined that the pressure signal output from the pressure transducer 640 is at about a predetermined pressure. In illustrative embodiments, the predetermined pressure is selected and the signal outputted, so that the imaging of the compressed tissue is started after the compression has reached an essentially steady state condition. While imaging is preferably not conducted during the transient period when the tissue 50 is transitioning from the uncompressed to compressed state, it should be recognized that the present invention is adaptable to collect image data during this transition period.

Figure 7:
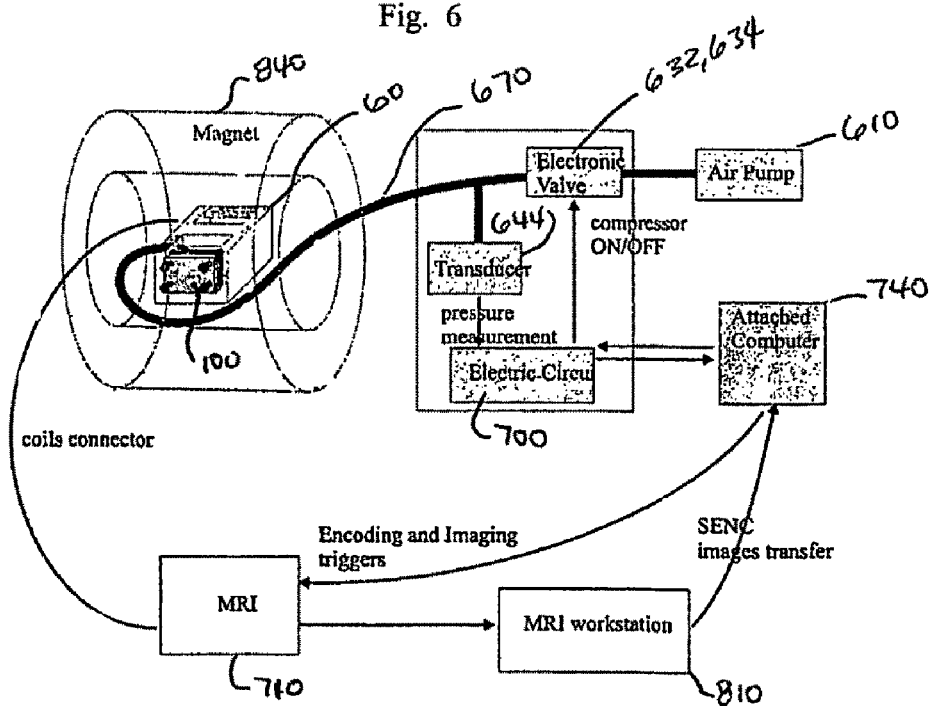
FIG. 7 is a schematic view of an illustrative integrated system according to the present invention.

Referring now to FIG. 7, there is shown a schematic view of an illustrative integrated system 800 according to the present invention including the structure 840 housing the MRI system main and gradient magnets or magnetic coils 840 as well as associated power and control circuitry, and an MRI workstation 810. The MRI workstation 810 is any of a number of workstations known to those skilled in the MRI arts where the image data from the acquired sequences of images can be processed and/or combined and so such image data can be displayed and/or stored.

As illustrated, the MRI detection coils 60 and a tissue compression device 100 are located within the structure 840 housing the MRI main and gradient magnets or magnetic coils 840 along with the subject to be imaged (not shown). As described herein, the moving mechanism 130 of the tissue compression device 100 is fluidly coupled using interconnecting tubing 679 to the fluid source 610 and to the first and second valves 632, 634. As also shown and described herein, these other portions of the fluid system 600 and the electrical and electronics module 700 are located outside of the structure 840 housing the MRI system magnets/magnetic coils. In illustrative embodiments, these other portions of the fluid system 600 and the electrical and electronics module 700 are located remote from such structure 840.

Figure 8:
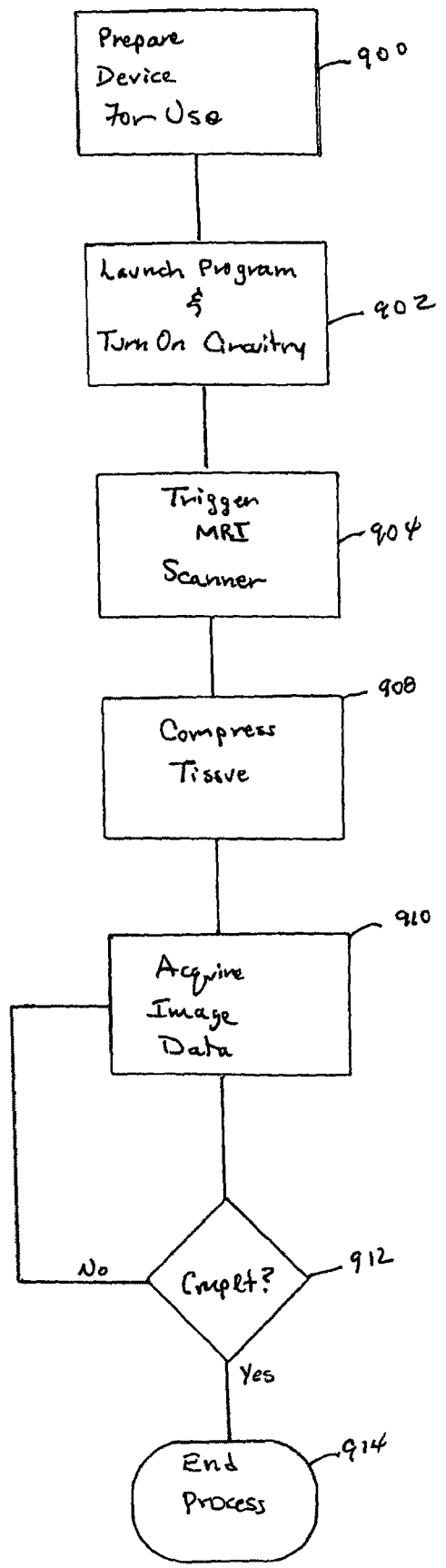
FIG. 8 is a flow diagram illustrating a methodology for acquiring image data according to the present invention.

Referring now to FIGS. 8 and 9, there is shown a methodology for acquiring image data according to the present invention (FIG. 8) and a graphical view showing the sequencing of MRI image acquisition and tissue compression (FIG. 9). Reference also shall be made to FIGS. 1-7 for features of the tissue compression device 100 and related fluid system 600 and electrical and electronics module 700 not otherwise shown in FIGS. 8 and 9, without requiring specific reference to be made to these other figures in the following discussion.

Initially the clinician or technician prepares the tissue compression device 100 for use with an MRI imaging technique, Step 900. Such preparation includes determining the compressive force limitations and appropriately configuring the tissue compression device 100, fluid system 600, and/or the electrical and electronics module 700 including the controller 740. For example, each of the stops 144 would be adjusted and tightened at a position corresponding to a maximum allowed displacement of the moveable member 110 with respect to the stationary member 120.

Also, such initial steps includes affixing or securing the tissue compressing device 100 to the MRI detection coil 60 (e.g., breast coil) and, if required, positioning and/or locating the moving mechanism 130 (e.g., airbag) so that the moveable member 110 moves responsive to actuation of the moveable member (e.g., expansion of the airbag). The technician also would assure that the fluid source is at or above a desired pressure level (e.g., 60-70 psi for a pneumatic fluid system).

The technician would then launch the applications program that controls the compression and image data acquisition process and turn on the appropriate circuitry, step 902. Prior to launching the program and as part of the initial preparatory actions, the technician can input desired control parameters including the timing of the tissue compression, data acquisition and the pressure level values.

The operator then would start the triggering of the scanner, step 904. For example, the technician could start triggering of the scanner by clicking a menu item "start trigger" being displayed for example on a display device visible to the operator. In particular embodiments, the MRI process embodies SENC imaging techniques. Thus, it is desirable to initiate the scanning process before compressing the tissue so that tissue tagging using the MRI technique occurs while the tissue is in the rest state (i.e., prior to tissue compression). Such a rest state is preferably an uncompressed tissue state or the normal state of tissue. It should be recognized, however, that it is within the scope of the present invention for the rest state to be a pre-compressed state in which tissue is pre-compressed for example, by causing the tissue compression device 100 to be positioned so that the moveable member 110 is compressing the tissue. The rest state and the tagging operations are illustrated in FIG. 9.

After triggering the MRI scanner and when the technician or operator is otherwise ready to proceed with image data acquisition, the tissue compression process is initiated, step 908. This can include having the technician opening the operator actuated switch 620 (preferably normally closed switch) and providing an input signal to the controller 740 that corresponds to an instruction to initiate the controlled actions necessary for the tissue compression device to compress the tissue. For example, the technician could use a computer mouse to press another menu item "compress" to initiate the process.

Such controlled actions includes outputting a signal so the first valve 632 is opened for a pre-specified time interval during which the moving mechanism causes the moveable member 110 to move thereby applying a compressive force to the tissue. As indicated above, the time interval can be changed in the computer program. At the end of the pre-specified time interval, the controller 740 preferably would output another signal causing the first valve 632 to close.

As described herein, either because of mechanical engagement of the safety stop with structure of the tissue compression device and/or because the first valve 632 is closed, further motion of the moveable member 110 is stopped thereby stopping further compression of the tissue 50. As shown in FIG. 9, the tissue compressive force varies as a function of time between the rest state to the fully compressed state which generally corresponds to the state where the moveable member is no longer moving away from the stationary member 120.

When the tissue is fully compressed and has again reached a steady state condition but in a compressed tissue state, the particular imaging technique is initiated whereby image data is acquired, step 910. In the case where the imaging technique embodies the SENC technique, a sequence of several image data acquisitions is acquired where one or more imaging parameters are modified so each data acquisition should be imaging the compressed tissue differently (e.g., at a different frequency). For example, once the tissue reaches the fully compressed state, a sequence of image data acquisitions with multi-demodulations is acquired.

As the present method allows the acquisition of one or more image data acquisitions, the method further includes determining if the data acquisition process is complete, Step 912. If data acquisition is not complete (No, Step 912), then the data acquisition process (Step 910) is continued. If the acquisition is complete (Yes, Step 912), then the imaging process for the given tissue is ended, Step 914. Such ending can include opening the second valve 634 as described herein to decrease the fluid pressure in the fluid system. When the fluid pressure is decreased, the moveable member 110 is no longer held in a displaced state away form the stationary member. Thus, the moveable member 110 can be moved back towards the stationary member 120, thereby also removing the compressive force on the tissue.

It also is possible that the volume of tissue to be imaged is can be large enough that the entire volume cannot be imaged in the time available (e.g., fading of the modulation (the tags) cause by the T1-relaxation effect). Thus, in such cases, the process described above in steps 902-912 would be repeated for the next slice or slices being imaged until the entire volume is imaged. It also is within the scope of the present invention for MRI technique being used and the parameters for the MRI to be adjusted so as to in turn adjust the thickness of the slice for which image data is being acquired during the time available.

SENC Imaging Technique

As suggested by the name, Strain Encoded (SENC) MRI is an imaging technique that is used to encode the images of tissue with information about tissue strain to reveal tissue deformation. The ability of the SENC technique to directly measure the tissue strain, rather than estimate it from displacement data, makes it unique among all MR imaging techniques. The technique was originally developed by Osman et al to image the regional deformation of the myocardium. N. F. Osman, S. Sampath, E. Atalar, J. L. Prince, "Imaging Longitudinal Cardiac Strain on Short-Axis Images Using Strain-Encoded (SENC) MRI," Magn. Reson. Med., vol. 46, pp. 324-334, 2001. Later, the technique was presented as a potential imaging technique that can detect the existence of stiff masses located inside a soft background matrix. Osman, NF, "Detecting stiff masses using strain-encoded (SENC) imaging," Magn. Reson. Med, vol. 49, pp. 605-608, 2003.

The SENC technique was originally developed as a modification of a traditional MR tagging technique, known as 1-1 SPAMM (Spatial Modulation of Magnetization). L. Axel, L. Dougherty, "MR imaging of motion with spatial modulation of magnetization," Radiology, vol. 171, pp. 841-845, 1989. Nevertheless, SENC imaging can be also considered a Stimulated Echo Acquisition Mode (STEAM) imaging technique due to the nature of the acquired echo. E. M. Haacke, R. W. Brown, M. R. Thompson, R. Venkatesan, Magnetic Resonance Imaging: Physical Principles and Sequence Design. New York: John Wiley & Sons, 1999. In fact, both perspectives are useful and needed to fully understand and develop the SENC technique.

The graphical plot shown in FIG. 9 also illustrates the imaging tissue stiffness in a single compression using SENC MRI although the technique can be adapted to image a large volume of tissue in successive tissue compressions. At the beginning, modulation/tagging pulses are applied while the object is at rest (uncompressed/pre-compressed state). Then, compression is applied to the surface of the object within a finite period of time (typically 300-1000 ms). Once the object becomes in a stationary compressed state, images with different demodulations are acquired. It can be seen in the figure that there is no repetition of the compression during that image acquisition process. This requires that compressing the object and imaging have to be carried out within a short period of time before the fading of the modulation (the tags) cause by the T1-relaxation effect. Since the T1-relaxation time is longer at higher magnetic fields (S. H. Duewell, T. L. Ceckler, K. Ong, H. Wen, F. A. Jaffer, S. A. Chesnick, and R. S. Balaban, "Musculoskeletal MR imaging at 4 T and at 1.5 T: comparison of relaxation times and image contrast," *Radiology*, vol. 196, pp. 551-5, 1995), using 3.0T scanners can be advantageous to such imaging technique.

EXAMPLE 1

SENC MRI

The Strain Encoded (SENC) MRI technique was introduced to measure local strain distribution of deforming tissues. In SENC MRI, the magnetization of the object under examination at point p and time t is modulated in the z-direction with a sinusoidal pattern with the spatial frequency, ω(p, t). The z-direction here is defined as the direction orthogonal to the imaging plane. Once induced, this pattern lasts for a fraction of a second, during which, if the tissue is deformed, the frequency ω(p,t) proportionally changes with the degree of deformation at the pixel p. The resulting image intensity at this pixel is given by $$I(\underline{p}, t) \approx \frac{1}{2}\rho(\underline{p}, t)S(\omega_T - \omega(\underline{p}, t)), \tag{1}$$

where p(p,t) is a term representing the proton density of the voxel including the T1 relaxation effect, S(ω) is the Fourier transform of the slice profile determined by the envelope of the applied slice selection RF pulse and $\omega_r$ is called the tuning frequency, which is determined during the image acquisition by an applied tuning gradient. The above equation shows that the function S(.) is shifted in proportion to the change in the tagging frequency ω(p,t), which depends on tissue deformation. Therefore, measuring this frequency allows the estimation of the tissue strain. It should be noted that this equation is valid only at reasonably high values of tagging frequencies with $\omega_T$ close to $\omega(p,t)$. The shift of the function S(.) can be estimated from the intensity of two images, $I_1(p,t)$ and $I_2(p,t)$, acquired with two different tuning frequencies, $\omega_{T1}$ and $\omega_{T2}$. That is, the tagging frequency at each pixel is estimated by the center-of-mass of the two image intensities using the following equation, $$\hat{\omega}(\underline{p}, t) = \frac{\omega_{T1} I_1(\underline{p}, t) + \omega_{T2} I_2(\underline{p}, t)}{I_1(\underline{p}, t) + I_2(\underline{p}, t)}. \quad (2)$$

This estimator yields an exact estimate of $\omega(p,t)$ under certain conditions. Since the distance between two points of tissue in the z-direction is inversely proportional to the frequency of the tagging pattern between them, the strain $\epsilon(p, t)$ can be calculated as, $$\varepsilon(\underline{p}, t) = \frac{\text{change in length}}{\text{original length(at } t = 0)} = \left( \frac{\omega(\underline{p}, 0)}{\omega(\underline{p}, t)} - 1 \right), \quad (3)$$

where $\omega(p,0)$ is the initial frequency of the applied tagging pattern (which is known a priori) and $\omega(p,t)$ is estimated from equation (2).

Tissue Tagging and Deformation

In order to induce a change in local frequency of the tagging lines, external deformation is applied only once, allowing the use of a simple compression tool. In the presented system, an airbag is attached tightly to the surface of the examined object (with a plate in between to ensure uniform pressure over the surface) and is used to provide deformation by an increase in the interior pressure. The pressure inside the airbag at steady state is about 2 psi. A three-way manual pneumatic valve is used to inflate or deflate the airbag by connecting its inlet to the pump or to the exhaust, respectively.

In order to synchronize imaging with the application of compression, a pressure transducer (#142PC05D, Honeywell Inc.) is used to convert the airbag pressure into an electric signal that is fed to a signal comparator (with hysteresis to provide noise immunity). As the rising pressure (hence the signal's voltage) exceeds a predetermined threshold (TH), a triggering signal is sent to the scanner to start the SENC pulse sequence. Upon the arrival of the triggering signal, a 1-1 Spatial Modulation of Magnetization (SPAMM) tagging sequence is played out to tag the tissue. As shown in FIG. 10, the pulse sequence tags the entire object with a sinusoidal pattern in the slice-selection (z-) direction using two non-selective 90° RF pulses and a gradient lobe in the z-direction.

Image Acquisition

Because the tagging pattern fades due to T1-relaxation effects, image acquisition should start shortly after tagging to maintain good SNR once tissue deformation has reached a steady state. In order to give the tissue a chance to be compressed and reach a steady state, a waiting period of 300 ms is applied before acquiring the strain-encoded (SENC) images of the compressed tissue. In order to accelerate the acquisition and avoid the need for multiple compressions, a segmented echo planar imaging (EPI) sequence is used (see FIG. 10). Rapidly switching gradient hardware enables the acquisition of one image with a resolution of 64×32 in less than 50 ms (frame rate>20 images/second). During acquisition, the flip angle for each excitation is incremented to ensure that the amount of excited magnetization remains fixed from one time frame to another. Rapid acquisition provided by the segmented EPI implementation makes it possible to acquire two images with two different tunings following the compression, with negligible effects from the fading of the tag lines. In order to reduce imaging artifacts, a dummy sequence is applied prior to acquiring the SENC images to establish steady state magnetization. The dummy sequence is the same as the SENC pulse sequence but without image reconstruction or display.

All experiments were done on a 1.5T Signa MR scanner (General Electric Medical Systems, Milwaukee, USA) using the segmented EPI pulse sequence and phased-array cardiac coil. Imaging parameters were TR/TE=12/1.6 ms, echo train length=8, slice thickness=10 mm, initial tag frequency=0.5 mm$^{-1}$, FOV=20 cm, and resolution=64×32.

Phantom Experiment

Figure 11A:
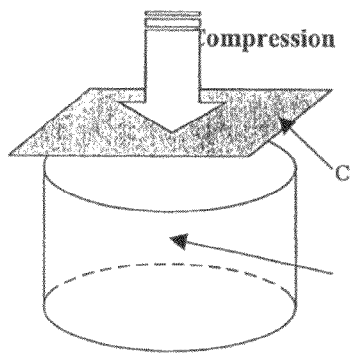
FIG. 11(a) is a 3D view of a phantom indicating the direction of compression and FIG. 11(b) is a cross-section of the gel phantom showing the stiffness of the discs, with gray levels indicating the relative stiffness from the softest (white) to the hardest (black)
Figure 11B:
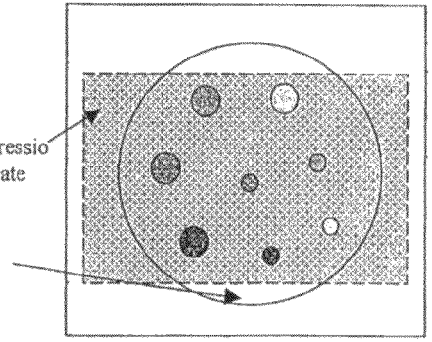

A gel phantom was built to test the ability of the system to obtain real-time strain images and also to test the sensitivity and the resolution of the technique. The silicon gel was prepared by mixing two compounds, A and B (kit 3-4150, Dow Corning), whose ratio in the mixer determines the stiffness of the resultant gel. A three dimensional (3-D) view of the phantom view is shown in FIG. 11 (*a*), which phantom contains two groups of small discs with two different sizes (16 and 7 mm in diameter and the same height 13 mm). Four discs of different stiffness from both groups (i.e., a total of 8 different mixes of the gel compounds) were immersed at a depth of 3.5 cm inside a larger cylinder (15 cm in diameter, 5 cm height) filled with a softer gel. FIG. 11(*b*) shows the location of the discs inside the phantom and assigns a name for each disc to make the reference to a particular disc easier. The compressing plate was rectangular in shape and shown as the rectangular shaded area in FIG. 11(*b*) such that some parts of the cylindrical phantom were not subjected to compression. This provides the advantage of testing the appearance of body regions that exist within the field-of-view (FOV) but are not subjected to the external compression. The applied pressure to the top of the phantom induced external deformation of 1.5 cm (strain=−1.5/5=−0.30).

Quantitative stiffness experiments were performed after the MR experiments. The quantitative stiffness values, represented by Young's modulus, of each of the eight disks and the background were measured using an indentation test. The test involved applying external deformation to the surface of each disc using a vertical cylinder (diameter=5 mm). The stress exerted by the cylinder was recorded with a force sensor (ATI Industrial Automation Inc.) at different strain levels. Then, the recorded stress-strain data were curve-fitted and the slope was calculated to determine the Young's modulus. The test was repeated at least two times for each disc and the maximum recorded variation for a measured value was about ±6 kPa. Table 1 shows the resulting Young's moduli of the discs at a strain level of 10%. According to previous studies on breast tissues, the soft gel in our phantom corresponds roughly to adipose tissue (Young's modulus of fat=9.9±5.7 kPa). In addition, the stiffness of the large and small discs are consistent with the reported range for glandular (=22.5±10.8 kPa) and some tumor tissues (=54 to 282 kPa).

TABLE 1

|  | D1 | D2 | D3 | D4 | E1 | E2 | E3 | E4 | BkGnd |
|---|---|---|---|---|---|---|---|---|---|
| Young's modulus | 73.75 | 57.51 | 48.65 | 21.43 | 91.45 | 70.2 | 51.28 | 24.5 | 10.35 |

Imaging Parameters of SENC MRI

In order to avoid interference from the signal caused by T1 relaxation effects, i.e. for equation (1) to be valid, the initial tagging frequency was set arbitrarily to 0.5 mm$^{-1}$ (any value greater than 2/L is sufficient). Based on this value, suitable values for the tuning frequencies can be determined to ensure a reliable estimate of strain. Imaging using a rectangular slice profile with a thickness of L(=10 mm) results in a k-space representation of a voxel as a sinc-function with the first zero-crossing located at 1/L mm$^{-1}$ (the k-space, also known as the spatial frequency space, is the Fourier transform of the spatial space). In this case, the tagging frequency, $\omega(p,t)$, can be exactly estimated using equation (2) if the following conditions are satisfied, $$(A) 0 \leq \omega(p,t) - \omega_{T1} \leq 1/L, \forall t,p \quad (4.a)$$

$$(B) \omega_{T2} - \omega_{T1} = 1/L \quad (4.b)$$

In order to satisfy condition (A), $\omega_{T2}$ and $\omega_{T1}$ can be taken, respectively, as the maximum and minimum expected value of $\omega(p,t)$ caused by tissue deformation. The minimum expected strain value can be assumed to be equal to −0.05 (contraction of 5%) since tissue stretching is of no importance in the current work. Using this assumption, equation (3) yields $\omega_{T1} = \omega(p,t)|_{min} \approx 0.53$ mm$^{-1}$. The maximum value of $\omega(p,t)$ can be roughly estimated assuming a linear decay of stress (and hence, strain) inside the phantom; given the boundary conditions (i.e., applied deformation) and the depth of the imaged phantom cross-section. In the phantom experiment, the applied maximum deformation was equal to −0.3, which gives maximum expected strain at a depth of 2.9 cm (cross section at the center of the discs) equal to −0.18. Using a more relaxed upper bound (=−0.20), equation (3) yields $\omega_{T2} = \omega(p,t)|_{max} \approx 0.62$ mm$^{-1}$. These values of tuning frequencies guarantee conditions (A) and (B) approximately and are sufficient to capture the expected range of deformations (−5% to −20%).

Image Display

Figure 12:
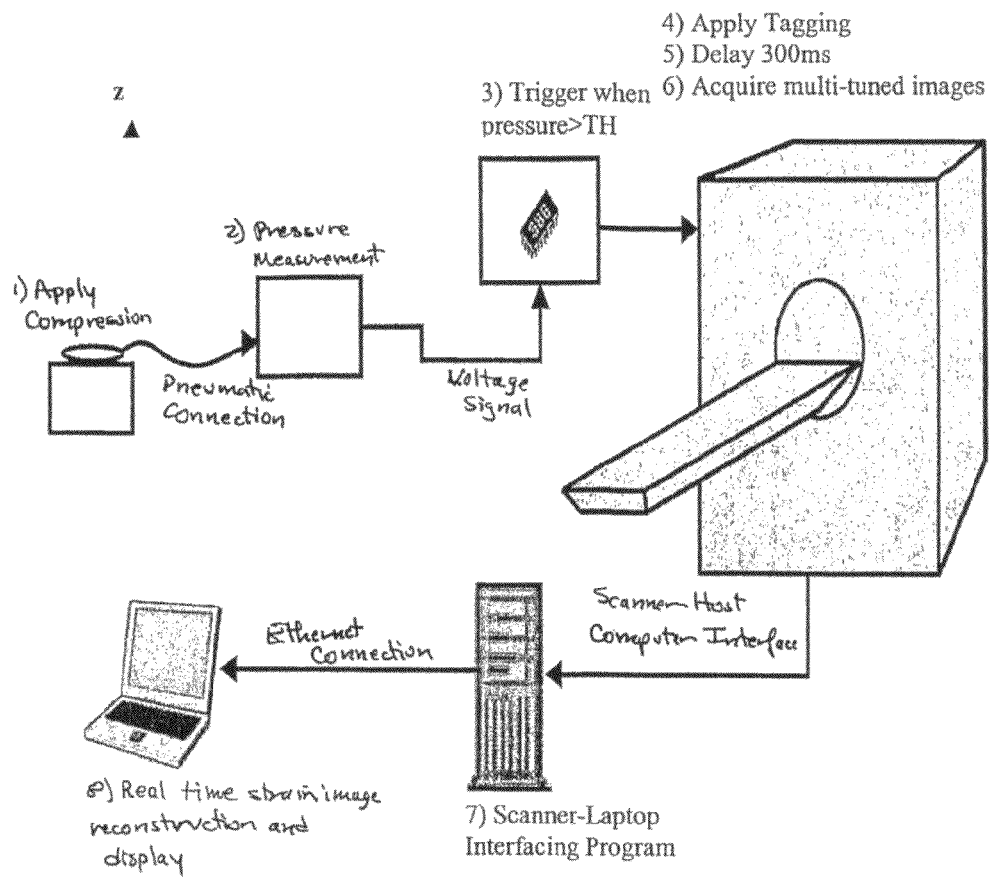
FIG. 12 is a schematic view of the elements of the entire system and the sequence of events indicated over each block, where the term TH refers to a predetermined pressure threshold slightly above the noise or the unintentional variation of the pressure inside the airbag.

After image acquisition, the current system allows real-time display of strain images on a PC (laptop) located outside the magnet room (latency of display is about 800 ms from the starting point of the pulse sequence). In order to display the images on the PC, the acquired k-space images at the two different tuning values are directly transferred from the scanner memory to the PC through an intranet connection (TCP/IP protocol at a transfer rate of 100M bps). Consequently, the transferred data is used to reconstruct and display the SENC images. Data transfer, processing, and display are achieved using an in-house program implemented in C++ code. The complete integrated system and the sequence of events are shown in FIG. 12.

Factors Influencing Stiffness Imaging

In SENC MRI, two factors may influence the ability of the technique to reflect the correct tissue stiffness contrast. The first factor is the mechanical limitation of visualizing stiffness based on a strain component in one direction only. This is a common limitation in ultrasound-based techniques as well, and has been studied before by Ophir et al. The other factor is the estimation error due to the signal noise and the incorrect selection of the imaging parameters. To demonstrate this effect, equation (1) was used to simulate signal intensity at different frequency shifts, i.e. different strain values, assuming unity amplitude, L=10 mm and $\omega(p,0)=0.5$ mm$^{-1}$. The simulated signal was then contaminated with white Gaussian noise (SNR=15 dB and 25 dB) and sampled at tuning frequencies of 0.5 and 0.6 mm$^{-1}$. In the simulation, the generated strain was allowed to go outside the predicted range (zero to 0.2 mm$^{-1}$ contraction) that was used to estimate the imaging parameters. FIG. 13 shows the resulting estimated strain versus the true strain (negative strains represent contraction). As shown in FIG. 13, the mean square error is low near the center of the predicted strain range and increases as the strain approaches the limits of this range. This can be explained by the low signal-to-noise ratio in one of the images, $I_1$ or $I_2$, at these extreme strain levels. For example, at a frequency shift of 1/L (or zero), the signal intensity of image $I_1$ (or $I_2$) will be identical to zero as described by equation (1), while the other image will assume maximum intensity. This extremely low SNR in one of the images makes the estimate more erroneous. At moderate strains, however, the signal intensities in both images $I_1$ and $I_2$ are reasonably high, and thus, the estimate becomes more robust. It can also be seen in the figure that a systemic error arises when the strain is outside the predicted range. However, unlike other MR imaging techniques that use phase encoding of motion, excessive deformation in SENC does not lead to phase wrapping and thus the estimated motion never drops to zero all at a sudden. To overcome this error, one should make sure that overestimation of the strain range is used when determining the imaging parameters.

Results and Discussion

Initially, two images were obtained without applying compression at tuning frequencies of 0.53 mm$^{-1}$ (FIG. 14(a)), and 0.62 mm$^{-1}$ (FIG. 14(b)). As shown in FIG. 14(a), the stiff discs cannot be distinguished from the surrounding material because they have almost the same T1/T2 parameters. In FIG. 14(b), there was no signal obtained from the phantom because the tuning used during acquisition was higher than the initially applied tagging frequency. In order to verify the ability of the system to capture the different deformation levels of the phantom material, compression was applied and images were acquired at the same tuning levels. Results for tuning frequencies of 0.53 and 0.62 mm$^{-1}$ are shown in FIGS. 15(a), (b), respectively. As expected, at low tuning frequency (0.53 mm$^{-1}$), only stiff discs appeared bright while the soft gel appeared dark. Finally, the two images were combined to construct a strain map as shown in FIG. 16.

Figure 17:
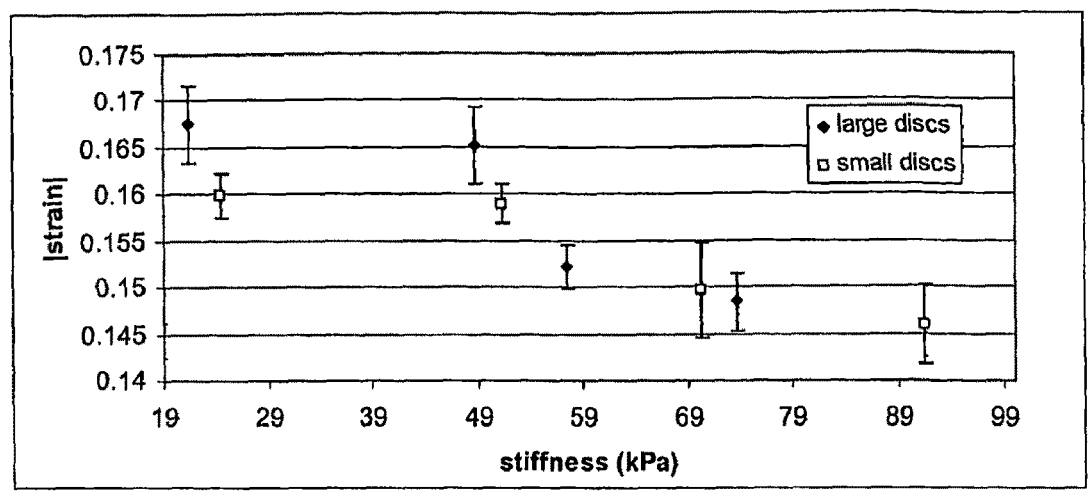
FIG. 17 is a graphical view of a scatter plot of the average strain values (±SD) inside the stiff inclusions acquired with the strain map versus their Young's modulus (kPa) as determined by the indentation test.

There is shown in FIG. 17 a graphical view of a scatter plot of the average strain values (±SD) inside the stiff inclusions acquired with the strain map versus their Young's modulus (kPa) as determined by the indentation test. FIG. 17 shows the strain values averaged over manually drawn circles within each disc. In order to determine the resolution of the acquired strain maps, the size of the discs was measured from the maps. First, the center of each disc was estimated by the coordinate mean of points sampled on its contour. Then, the radius of the disc was approximated by the average distance between the sampled points and the estimated disc center. Radius calculations are listed in Table 2, where two observations can be made. First, the calculated diameters of the discs are larger than the actual values. Second, the amount of the diameter overestimation increases, in general, with the disc stiffness except for the disc with the least stiffness in the small disc group.

TABLE 2

| GROUP I (LARGE) | Diameter | GROUP II (SMALL) | Diameter |
|---|---|---|---|
| D1 (Stiffest) | 20.12 ± 1.65 | E1 (Stiffest) | 14.71 ± 1.26 |
| D2 | 19.801 ± 1.07 | E2 | 12.68 ± 0.96 |
| D3 | 17.52 ± 2.26 | E3 | 10.41 ± 1.11 |
| D4 (Softest) | 16.31 ± 1.69 | E4 (Softest) | 12.25 ± 2.08 |

The SENC imaging system enabled the imaging of existing masses in the phantom based on the local strain of the masses relative to the surrounding material even when such masses were not detected by conventional MR imaging techniques. The strain map illustrates the ability of the technique to identify the presence of the stiff inclusions. Moreover, pair-wise comparisons of the average strain of the individual discs showed a significant difference between each pair of discs (almost zero p-value for all pairs except the pair with the least stiffness within the same disc group (large or small), where a p-value of 0.01 was noticed). As shown in FIG. 17, when comparing discs of same size, the local average of the measured strain can order the discs based on their Young's modulus. If discs of different sizes are to be compared, then inconsistency can be noticed at disc E4, which has average strain less than that of Disc D3. This may be due to its low stiffness relative to the background material of the phantom and the overall low SNR of the image.

Figure 18A:
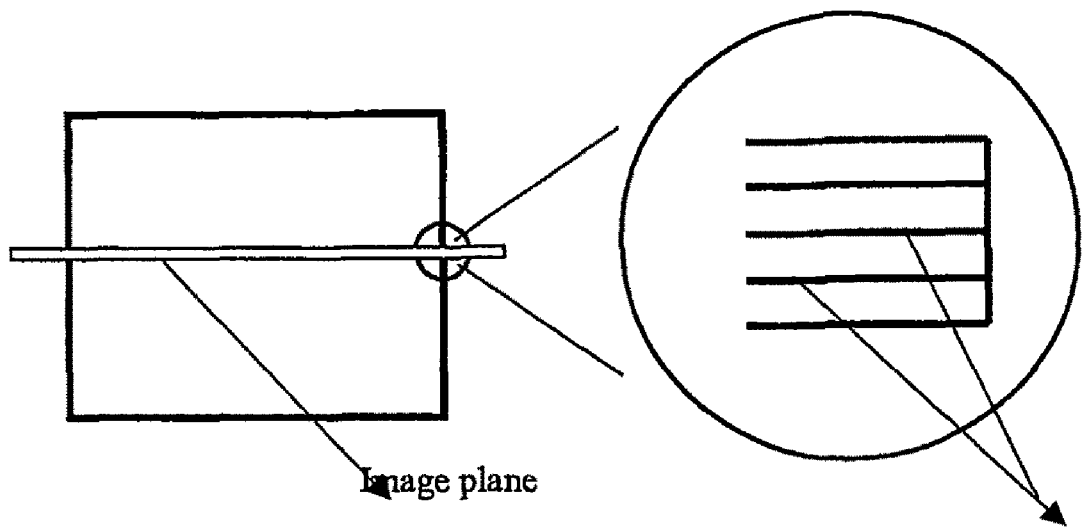
FIGS. 18(a),(b) are side views of the phantom before (FIG. 18(a)) and after compression (FIG. 18(b)), where compression leads to extrusion of the phantom boundaries, which causes the tagging separation at the phantom boundaries to be higher than that in the phantom interior.
Figure 18B:
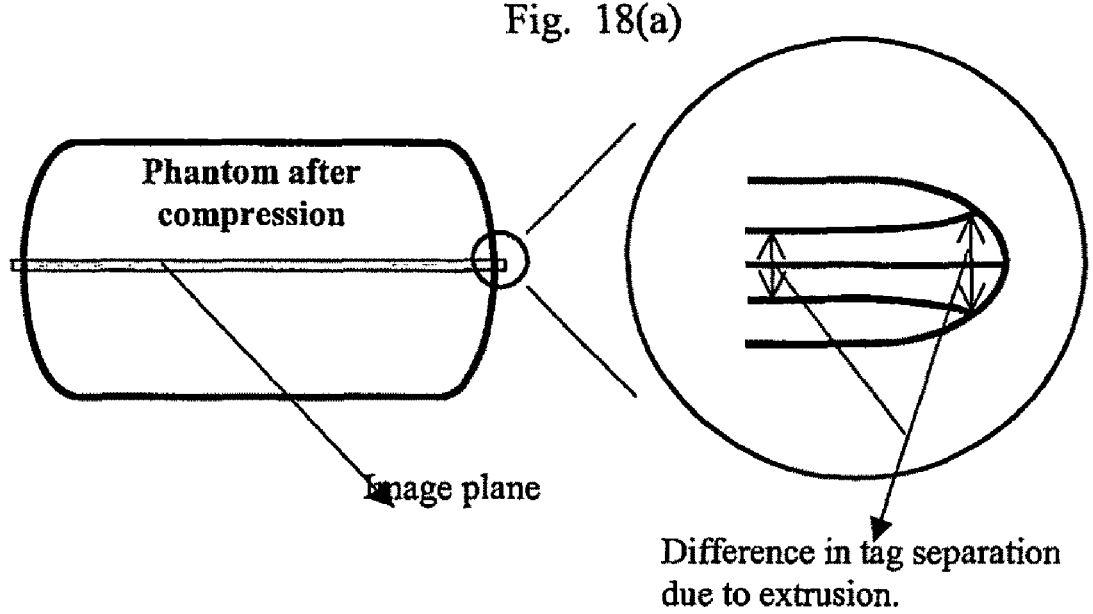

It can be observed from the strain map in FIG. 16 that the phantom boundaries show low deformation despite low stiffness. The reason for this is the extrusion of the sides of the phantom caused by their free boundary conditions while the upper and lower faces are constrained by the compressing plates, as shown in FIGS. 18(*a*),(*b*) respectively. This extrusion maintains the separation between the tag lines in the through-plane direction unchanged at the boundaries, which, therefore, appear as low strain in the map. Furthermore, due to the rectangular shape of the compressing plate, the two sides of the phantom that are not covered by the compressing plate are free to undergo stretching through extrusion. But since stretching was not considered when the tuning values were determined, the phantom sides that are stretched do not appear in the acquired images and give the appearance that the phantom was trimmed (arrow heads in FIG. 15(*a*).

The overestimation of the disc diameters in Table 1 can be related to the continuity of the tag lines, which prevents abrupt changes in spatial frequency—from low frequency inside the disc to high frequency in the immediately adjacent soft material. Therefore, regions adjacent to the discs appear to be less compressed on the SENC images. This increase in regions of low strain is enhanced by the partial volume effect resulting from low resolution imaging. Subsequently, it is expected that the degree of overestimation increases proportionally to the strain difference between a disc and its surrounding soft material, as seen in Table 2—with the exception of the small softest disc. The reason for this inconsistency can be attributed to the limitation of the technique at low imaging SNR and low resolution, complicated by the low stiffness of that disc. The overestimation of the size of small discs can be considered advantageous, as it improves the chances of detecting small stiff masses—including those of subpixel size.

The use of cardiac phased-array coils, which are designed to pick up signal based on the chest geometry rather than the phantom, is not optimal and it is conceivable that better SNR can be obtained by using dedicated coils optimized for a specific organ. Moreover, a possible gain in SNR may be obtained using a Steady State Free Precession (SSFP) sequence or by using the average of more than one image (increased number of excitations) for each tuning. Preliminary results for the implementation of SSFP sequence with SENC MRI can be found in E. Ibrahim, N. F. Osman, "A Technique for Improving Tag Contrast Persistence in SSFP MRI Imaging Using Adaptive Flip Angle," IEEE Conf. Proc. Int. Sym. Biomed. Imag. (ISBI), pp. 1051-1054, 2004.

Finally, the applied external deformation was relatively high (at least 5 times the applied deformation in ultrasound elastography). This provides the advantage of increased the stiffness contrast between the different tissues as shown by Krouskop (T. A. Krouskop, T. M. Wheeler, F. Kallel, B. S. Garra, T. Hall, "The elastic moduli of breast and prostate tissues under compression," *Ultrason. Imaging*, vol. 20, pp. 151-159, 1998). Such a high compression level was possible because, unlike ultrasound-based techniques, high deformation does not distort the measured signal. However, although such high deformation is reasonable for some organs, such as the breast—which is usually exposed to an even higher level of compression in regular x-ray mammography, it may not be practically suitable for other organs. In such situation, the imaging parameters should be modified (e.g., increase the tagging frequency) to match favorable lower strain levels.

EXAMPLE 2

Figure 19:
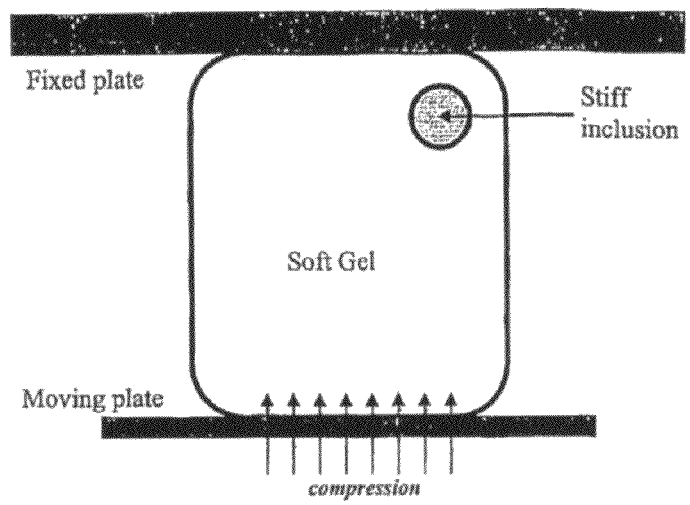
FIG. 19 is a top view of a phantom composed of a small stiff sphere 1 cm in diameter immersed in a cube made from softer gel material.

A phantom experiment was used in order to test the tissue compression device of the present invention. The phantom was made of a silicon gel material prepared by mixing two compounds, A and B (kit 3-1450, Dow Corning). The ratio in the mixture determines the stiffness of the resultant gel: The phantom was composed of a small stiff sphere 1 cm in diameter immersed in a cube made from softer gel material with dimensions 8×8×10 cm$^3$. A top-view of the phantom is shown in FIG. 19. It is worth noting that the stiff inclusion was intentionally placed near the corner of the phantom to test the ability of the system to detect lesions at the periphery of the breast (difficult situation). The stiffness of the inclusion was made very close to that of the surrounding soft gel. In fact, manual palpation on the surface of the phantom did not detect the existence of the inclusion.

Image Acquisition

The phantom experiment was done on a 3.0T MR scanner (Achieva, Philips Medical Systems, Best, Netherlands): The imaging parameters were: spiral acquisition with 9 interleaves, TE/TR=0.9/14.62 ms, slice thickness=10 mm, FOV=350 mm, and a ramped flip angle with maximum=45°. The total acquisition time for each demodulated image was 180 ms (9×TR+delay time imposed by the scanner to reduce the SAR level). It is worth noting that this poor temporal resolution did not affect the image quality because the phantom is imaged while it is at steady state. The initial tag (or modulation) frequency was 0.3 mm$^{-1}$ and the demodulation frequencies (N=8) were ramped linearly from 0.3 to 0.4 mm$^{-1}$. The pause time between the modulation pulse and the start of the acquisition was 1000 ms which was appropriate to allow enough time for the airbag to reach steady state fully compressed state (the pressure inside the compressor tank was 70 psi).

Results and Discussion

Figure 20:
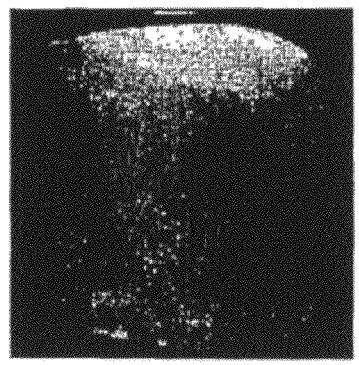
FIG. 20 is classical T1-weighted image of the phantom taken at the plane of the inclusion.

A classical T1-weighted image of the phantom taken at the plane of the inclusion is shown in FIG. 20. It can be noticed that the contrast between the inclusion and the surrounding phantom material is quite low. The arrow head in the figure indicates the location of the stiff inclusion.

Figure 21:
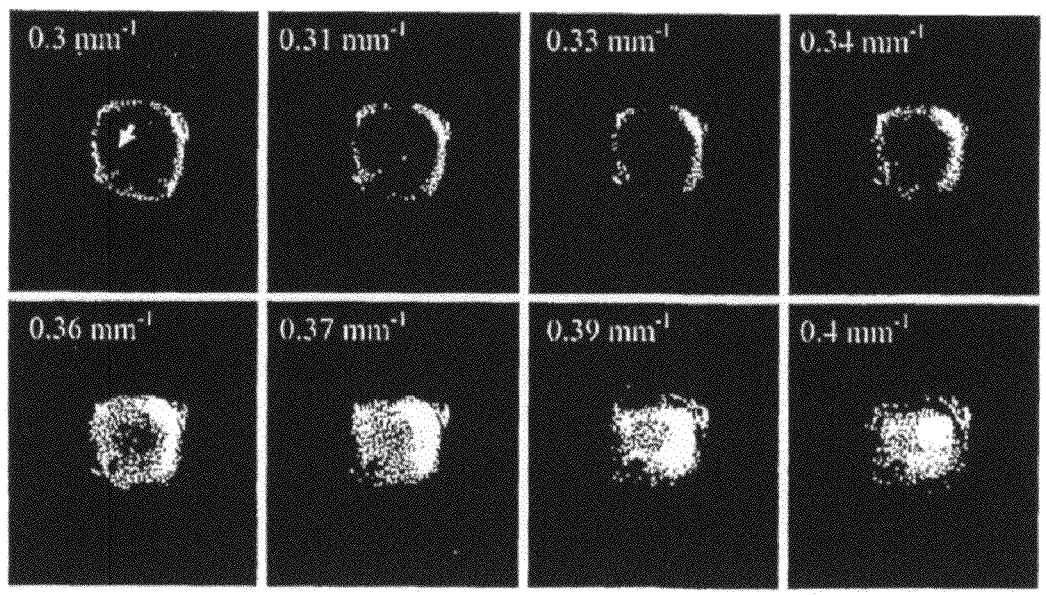
FIG. 21 provides eight images acquired using the SENC MRI technique with eight different demodulation frequencies.
Figure 22:
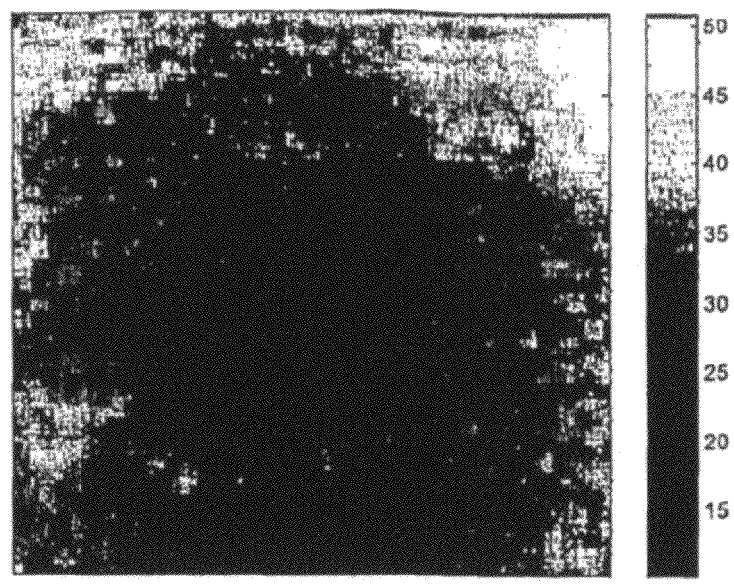
FIG. 22 illustrates the SNR of the SENC images of FIG. 11.

The acquired SENC images (eight images acquired with eight different demodulation frequencies) of the same cross section are shown in FIG. 21. It can be noticed that the stiff inclusion appears bright at low demodulation values and dark at high demodulations. The arrow head points to the location of the stiff inclusion. The situation is reversed for the soft background with exception at the phantom borders due to the extrusion effect described in the previous chapter. The SNR of the SENC images is shown in FIG. 22.

Figures 23A, 23B:
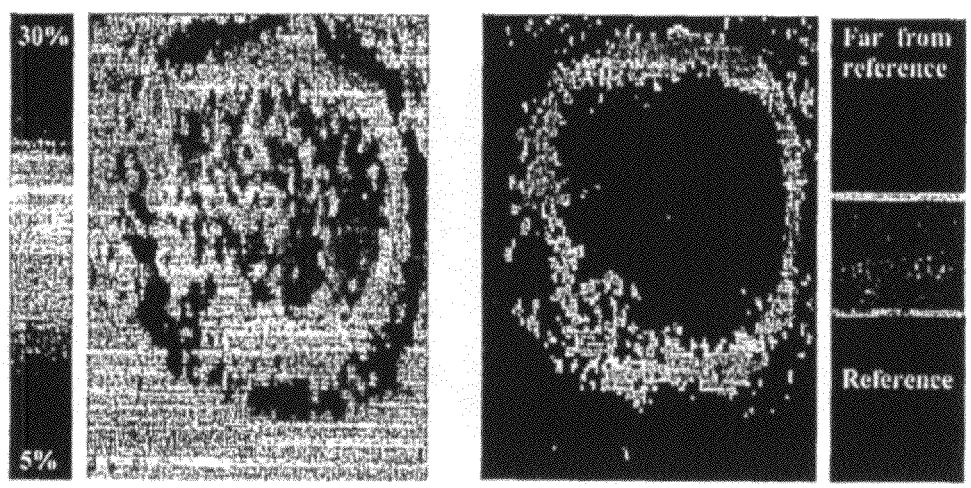
FIG. 23(a) is an illustration of a strain map.
FIG. 23(b) is an illustration of an image yielded when applying an ISODATA clustering algorithm to the acquired SENC images of FIG. 21.

The range of the SNR shown in the figure (15-50 dB) suggests that strain estimation is best achieved using the curve-fitting method with the 1-parameter model. The strain map that results from the curve fitting estimator is shown in FIG. 23(a). It can be seen that the inclusion has low strain (5-10%) relative to the surrounding gel material (20-30%). As mentioned before, the borders of the phantom shows less strain due to the extrusion effect. Because the inclusion was close to the phantom borders, exact delineation of its boundaries is difficult. However, in practical situation, once a lesion is suspected, the scan can be repeated at higher spatial resolution to zoom into the suspected region.

Applying an ISODATA clustering algorithm to the acquired SENC images yielded the image shown in FIG. 23(b), which contains 5 clusters of pixels. The parameters of the ISODATA algorithm were as follows. The number of iterations was 50, minimum number of members/cluster ($N_{MIN}$)=1, desired number of clusters ($N_D$)=5, maximum allowed intracluster variance ($\sigma^2_s$)=0.1, maximum separation for merging ($D_{MERGE}$)=0.01 and maximum number of clusters that can be merged in one iteration ($N_{MERGE}$)=3. It is interesting to see that clustering of the images reveals more distinction between the inclusion and the surrounding soft gel. This could be attributed to the special features of the inclusion boundaries that is different form those of its interior. Another interesting observation is that the background noise has been divided into two clusters each has a different distance from the reference cluster.

As can be seen from the foregoing, the tissue compression device of the present invention is based on a simple idea of providing a mechanism such as an airbag between two plates with one of them fixed while the other is free to move against the breast. The operation of such a tissue compression device is accompanied by a number of mechanical, pneumatic, electrical and manual safeguards. The operation and control of the device is achieved by a software program running on a controller or computer that can be located in the console room of the MRI scanner. The software program takes care of synchronizing the compression with the imaging pulse sequence. The imaging system as a whole replicates the simple and conventional palpation method to induce tissue deformation and provides sensitive MR imaging to measure this deformation. The imaging system of the present invention is particularly suitable to detect tissue lesions and to characterize tissues based on their relative stiffness.

Although a preferred embodiment of the invention has been described using specific terms, such description is for illustrative purposes only, and it is to be understood that changes and variations may be made without departing from the spirit or scope of the following claims.

Incorporation By Reference

All patents, published patent applications and other references disclosed herein are hereby expressly incorporated by reference in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A device for selectively compressing target tissue for magnetic resonance imaging of the target tissue, said compression device comprising:
    a moveable member including a contact surface that is configured to contact the target tissue and a non-contact surface disposed opposite the contact surface;
    a stationary member disposed opposite and substantially parallel to the non-contact surface of the movable member:
    a member moving mechanism operably coupled to the moveable member and operatively coupled to the stationary member such that a space is defined between the non-contact surface of the moveable member and the stationary member, the mechanism including moving means for moving the moveable member with respect to a fixed surface disposed opposite to the moveable member contact surface, whereby the target tissue is compressed between the moveable member contact surface and the fixed surface; and
    wherein the moveable member, the stationary member, and the member moving mechanism are made of MRI-compatible materials.

2. The compression device of claim 1, wherein the fixed surface is one a surface of a second stationary plate, a surface of a skeletal structure or a surface of a structure of an MRI detection coil.

3. The compression device of claim 1, wherein the moving means is a fluid moving means that causes the moveable member to move with respect to the fixed surface responsive to application of fluid pressure to the fluid moving means.

4. The compression device of claim 3, wherein the moving mechanism includes a force limiting mechanism that limits the compressive force being applied to the target tissue.

5. The compression device of claim 4, wherein the force limiting mechanism is a fluid device that limits a maximum fluid pressure developed for compression.

6. The compression device of claim 4, wherein the force limiting mechanism includes one or more sliding members secured to the moveable member; one or more through apertures in the fixed member, one aperture for each of the one or more sliding members, wherein the sliding members and the fixed member through apertures are arranged so that each sliding member is slidably received in a through aperture; a stop affixed to at least one of the one or more sliding members, the stop being affixed to the sliding member so as to be a predetermined distance from the moveable member, the predetermined distance being established so the force being applied to the target tissue during compression is less than or equal to a desired value.

7. The compression device of claim 6, wherein the stop affixed to at least one of the one or more sliding members is disposed opposite to a back surface of the stationary member, whereby when the stop contacts the back surface further sliding movement of sliding members is restrained thereby stopping movement of the moveable member.

8. The compression member of claim 6, further comprising a plurality of sliding members.

9. The compression member of claim 8, further comprising a plurality of stops, a stop being affixed to each sliding member.

10. The compression device of claim 3, further comprising a pressure sensor that senses pressure of the fluid.

11. The compression device of claim 1, wherein the moving means includes one or more expandable members disposed between the moveable member and the stationary member, each of the one or more expandable members being configured so as to expand primarily in one direction when fluid pressure within each expandable member is increased.

12. The compression device of claim 11, wherein the fluid is a gas.

13. The compression device of claim 1 further comprising a controller being configured to control operation of the member moving mechanism and for providing one or more output signals as input to the MRI process.

14. The compression device of claim 13, wherein the moving means includes one or more expandable members disposed between the moveable member and the stationary member, each of the one or more expandable members being configured so as to expand primarily in one direction when fluid within each expandable member is increased and wherein the controller controls flow of fluid to each of the one or more expandable members.

15. The compression device of claim 14, wherein the controller is configured to cause fluid flow to each of the one or more expandable members to move the moveable member with respect to the stationary member and to terminate fluid flow when a desired expansion of the one or more expandable members is achieved so as to maintain the pressure in each of the one or more expandable members.

16. The compression device of claim 15, wherein the controller is configured so as to cause fluid to flow from each of the one or more expandable members, so as to thereby reduce the compressive force on the target tissue.

17. The compression device of claim 1 further comprising removable fasteners for securing the compression device to a breast-coil MRI device.

18. A system for imaging target tissue of a patient, said system comprising:
a magnetic resonance imaging (MRI) apparatus that images the target tissue using magnetic resonance imaging techniques;
a tissue compression device that selectively compresses the target tissue, said compression device including:
a stationary member,
a moveable member including a contact surface that is configured to contact the target tissue,
a member moving mechanism having a first end operably coupled to the moveable member and having a second end operatively coupled to the stationary member, such that a space is defined between the moveable member and the stationary member, the mechanism including moving means for moving the moveable member with respect to the stationary member and to a fixed surface disposed opposite to the moveable member contact surface, whereby the target tissue is compressed between the moveable member contact surface and the fixed surface, and
wherein the moveable member and the member moving mechanism are made of MRI-compatible materials; and
a controller operably coupled to the tissue compression device and the MRI apparatus, the controller being configured to control operation of the member moving mechanism and for providing one or more output signals as input to the MRI process so the compressed targeted tissue is imaged during a compressed tissue condition.

19. A method for imaging tissue; comprising the steps of:
providing a tissue compression device that selectively compresses target tissue, said compression device including:
a stationary member,
a moveable member including a contact surface that is configured to contact the target tissue, and
a member moving mechanism operably coupled to the moveable member and to the stationary member, such that a space is defined between the stationary member and the moveable member, the mechanism including moving means for moving the moveable member with respect to the stationary member and to a fixed surface disposed opposite to the moveable member contact surface, wherein the moveable member and the member moving mechanism are made of MRI-compatible materials;
disposing the target tissue between the fixed surface and the moveable member;
compressing the target tissue between the fixed surface and the moveable member;
providing an output signal to an MRI imaging apparatus so image data is acquired after a tissue compressed condition is established; and
acquiring one or more sequences of image data of the compressed target tissue using an MRI imaging technique (MRI), one or more of MRI imaging parameters being: adjusted so as to be different for each of the one or more sequences of image data being acquired.

* * * * *